(12) United States Patent
Lee et al.

(10) Patent No.: US 12,198,348 B2
(45) Date of Patent: Jan. 14, 2025

(54) COMPUTERISED TOMOGRAPHY IMAGE PROCESSING

(71) Applicant: Oxford University Innovation Limited, Oxford (GB)

(72) Inventors: Regent Lee, Oxford (GB); Anirudh Chandrashekar, Oxford (GB); Vicente Grau, Oxford (GB); Ashok Handa, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 410 days.

(21) Appl. No.: 17/637,259

(22) PCT Filed: Aug. 21, 2020

(86) PCT No.: PCT/GB2020/052014
§ 371 (c)(1),
(2) Date: Feb. 22, 2022

(87) PCT Pub. No.: WO2021/038203
PCT Pub. Date: Mar. 4, 2021

(65) Prior Publication Data
US 2022/0284583 A1    Sep. 8, 2022

(30) Foreign Application Priority Data

Aug. 23, 2019 (GB) .................................... 1912150
Feb. 10, 2020 (GB) .................................... 2001791
Feb. 10, 2020 (GB) .................................... 2001792

(51) Int. Cl.
*G06N 3/08* (2023.01)
*G06T 7/00* (2017.01)
(Continued)

(52) U.S. Cl.
CPC .............. *G06T 7/11* (2017.01); *G06T 7/0012* (2013.01); *G06V 10/774* (2022.01); *G16H 30/20* (2018.01);
(Continued)

(58) Field of Classification Search
CPC ......... A61B 34/37; A61B 34/20; A61B 34/10; A61N 2/006; G06T 7/62; G06T 7/11; G06T 19/003; G06T 19/006
See application file for complete search history.

(56) References Cited

U.S. PATENT DOCUMENTS 10,163,040 B2    12/2018 Poole et al.
2010/0067760 A1*    3/2010 Zhang ..................... G06T 7/143
382/130

(Continued)

FOREIGN PATENT DOCUMENTS

WO    2018/208927 A1    11/2018
WO    2018/236905 A1    12/2018
(Continued)

OTHER PUBLICATIONS

International Search Report and Written Opinion for WO 2021/038203 (PCT/GB2020/052014), dated Jan. 15, 2021, pp. 1-15.
(Continued)

*Primary Examiner* — Phuoc H Doan
(74) *Attorney, Agent, or Firm* — Thomas|Horstemeyer, LLP

(57) ABSTRACT

A method for training a machine learning image segmentation algorithm to segment structural features of a blood vessel in a computed tomography (CT) image is described herein. The method comprises receiving a labelled training set for the machine learning image segmentation algorithm. The labelled training set comprising a plurality of CT images, each CT image of the plurality of CT images (Continued)

showing a targeted region of a subject, the targeted region including at least one blood vessel. The labelled training set further comprises a corresponding plurality of segmentation masks, each segmentation mask labelling at least one structural feature of a blood vessel in a corresponding CT image of the plurality of CT images. The method further comprises training a machine learning image segmentation algorithm, using the plurality of NCT images and the corresponding plurality of segmentation masks, to learn features of the CT images that correspond to structural features of the blood vessels labelled in the segmentation masks, and output a trained image segmentation model. The method further comprises outputting the trained image segmentation model usable for segmenting structural features of a blood vessel in a CT image. Further methods are described herein for using the trained image segmentation model to segment structural features of blood vessels, and to establish the training set for training the machine learning image segmentation model. Computing apparatuses and computer readable media are also described herein.

16 Claims, 32 Drawing Sheets

(51) Int. Cl.
  *G06T 7/11* (2017.01)
  *G06V 10/774* (2022.01)
  *G16H 30/20* (2018.01)
(52) U.S. Cl.
  CPC ............... *G06T 2207/10081* (2013.01); *G06T 2207/20021* (2013.01); *G06T 2207/20081* (2013.01); *G06T 2207/20084* (2013.01); *G06T 2207/30048* (2013.01); *G06T 2207/30101* (2013.01)

(56) References Cited

U.S. PATENT DOCUMENTS

| 2011/0224542 A1 | 9/2011 | Mittal et al. |
| 2020/0294288 A1 | 9/2020 | Smith |

FOREIGN PATENT DOCUMENTS

| WO | 2019/155306 A1 | 8/2019 |
| WO | 2020/186208 A1 | 9/2020 |

OTHER PUBLICATIONS

UK Search Report for GB 1912150.8, dated Feb. 18, 2020, pp. 1-10.
Ravichandran Savitha Rani et al: "3D Inception U-Net for Aorta Segmentation using Computed Tomography Cardiac Angiography", 2019 IEEE EMBS International Conference on Biomedical & Health in Format i cs ( BH I) , IEEE, May 19, 2019 (May 19, 2019), pp. 1-4.
Jian-Qing Zheng et al: "Abdominal Aortic Aneurysm Segmentation with a Small Number of Training Subjects", arxiv.org, Cornell University Library, 201 Olin Library Cornell University Ithaca, NY 14853, Apr. 9, 2018 (Apr. 9, 2018).
Karen Lopez-Linares et al: "3D convolutional neural network for abdominal aortic aneurysm segmentation", arxiv.org, Cornell University Library, 201 Olin Library Cornell University Ithaca, NY 14853, Mar. 3, 2019 (Mar. 3, 2019).
European Exam Report for Patent Application No. 20 764 733.0, dated Sep. 27, 2024, pp. 1-9.
Jen-Tang Lu et al: "DeepAAA: clinically applicable and generalizable detection of abdominal aortic aneurysm using deep learning", arxiv.org, Cornell University Library, 201 Olin Library Cornell University Ithaca, NY 14853, Jul. 4, 2019 (Jul. 4, 2019).
Marie Bieth et al: "Segmentation of Skeleton and Organs in Whole-Body CT Images via Iterative Trilateration", IEEE Transactions on Medical Imaging, vol. 36, No. 11, Nov. 1, 2017 (Nov. 1, 2017), pp. 2276-2286.
Noothout et al., "Automatic Segmentation of Thoracic Aorta Segments in Low-Dose Chest CT", Image Sciences Institute, University Medical Center Utrecht, Utrecht, The Netherlands, Oct. 9, 2018, pp. 1-6.

* cited by examiner

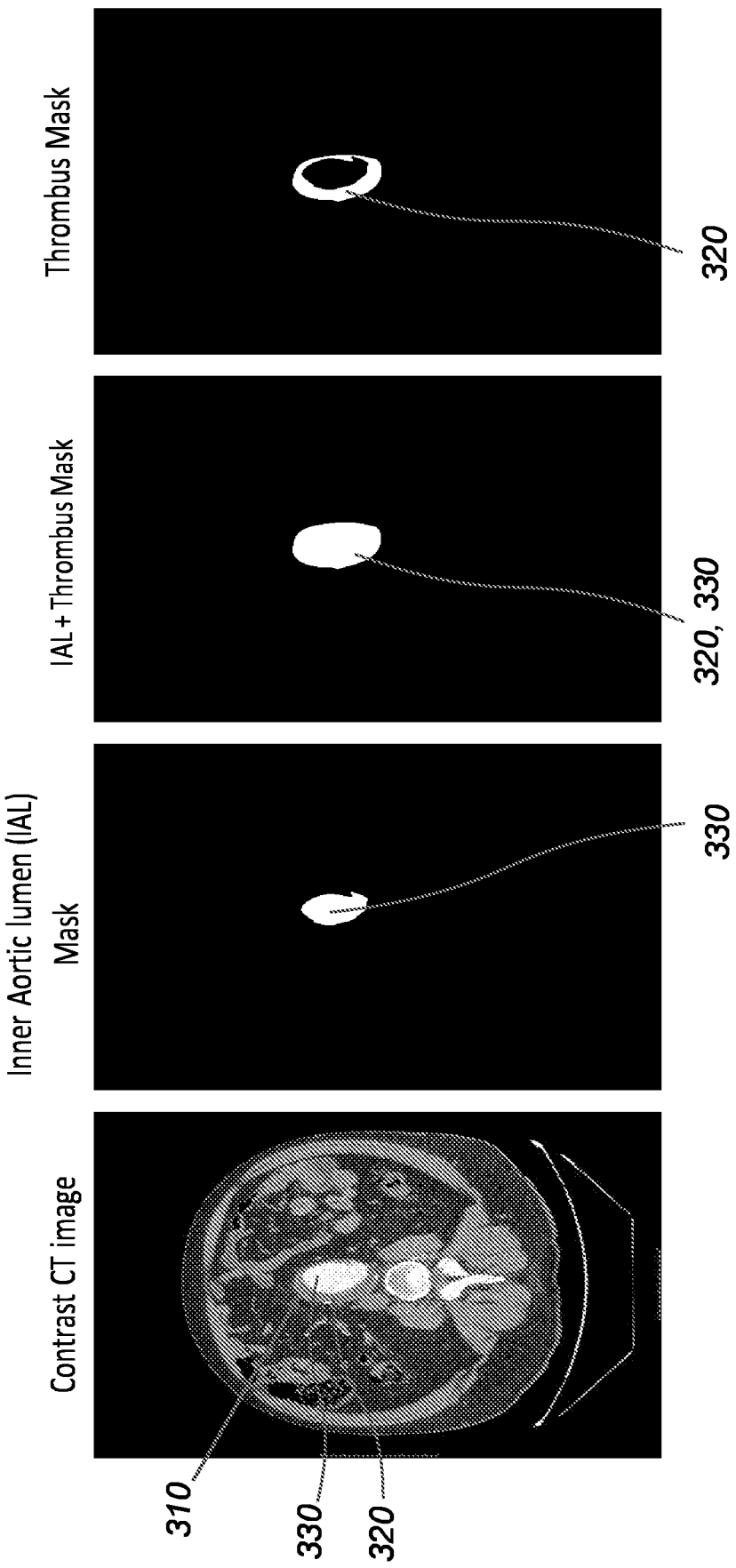

|  | Model Training | | Model Evaluation |
|---|---|---|---|
|  | Training Cohort ($n_{train}$) | Validation Cohort ($n_{valid}$) | Testing cohort ($n_{test}$) |
| Patients | 10 | 3 | 13 |
| Post-Augmented Scans | 110 | 33 | .. |

| Model | Epochs | Goal |
|---|---|---|
| U-Net | 1000 | Multi-Class AAA Segmentation |
| Attn U-Net | 1000 | Multi-Class AAA Segmentation |
| Attn U-Net A | 600 | Aortic Segmentation from low-resolution isotropic CTA |
| Attn U-Net B | 1500 | Multi-Class Aortic Arch Segmentation from high-resolution isotropic CTA |
| Attn U-Net C | 1500 | Multi-Class Descending Aorta + AAA Segmentation from high-res. isotropic CTA |
| Attn U-Net D | 600 | Aortic Segmentation from low-resolution isotropic Non-Contrast CT |
| Attn U-Net E | 600 | Aortic Segmentation from high-resolution isotropic Non-Contrast CT |

FIG. 17

| | Training Cohort (n=13) | | Test Cohort (n=13) | | p-value |
|---|---|---|---|---|---|
| Contrast | | | | | |
| 25th Percentile HU [95% CI] | -1008 | [-1003 -1014] | -1006 | [-1002 -1010] | 0.42 |
| Mean HU [95% CI] | -587 | [-646.1 -527.6] | -568.4 | [-610.2 -526.6] | 0.48 |
| 75th Percentile [95% CI] | -67 | [-45.8 -85.8] | -54.1 | [-40.8 -67.4] | 0.18 |
| Standard Deviation [95% CI] | 484.1 | [475.0 493.2] | 490.6 | [485.1 495.9] | 0.08 |
| Voxel Length [95% CI] | 0.81 mm | [0.76 0.86] | 0.83 mm | [0.79 0.87] | 0.50 |
| Voxel Height [95% CI] | 0.81 mm | [0.76 0.86] | 0.83 mm | [0.79 0.87] | 0.50 |
| Voxel Thickness | 1.25 mm | | 1.25 mm | | - |
| KVP | 120 | | 120 | | - |
| Exposure Time [95% CI] | 434 | [359.2 508.8] | 474.2 | [369.3 579.0] | 0.50 |
| Non-Contrast | | | | | |
| 25th Percentile HU [95% CI] | -1009 | [-1005 -1013] | -1005 | [-1002 -1008] | 0.07 |
| Mean HU [95% CI] | -565 | [-524.3 -606.7] | -550.6 | [-589.4 -511.9] | 0.55 |
| 75th Percentile [95% CI] | -53.4 | [-39.9 -66.9] | -46.8 | [-622 31.3] | 0.49 |
| Standard Deviation [95% CI] | 483.2 | [476.0 490.0] | 484.8 | [479.8 489.9] | 0.69 |
| Voxel Length [95% CI] | 0.80 mm | [0.75 0.85] | 0.82 mm | [0.78 0.86] | 0.58 |
| Voxel Height [95% CI] | 0.80 mm | [0.75 0.85] | 0.82 mm | [0.78 0.86] | 0.58 |
| Voxel Thickness | 2.5 mm | | 2.5 mm | | - |
| KVP | 120 | | 120 | | - |
| Exposure Time [95% CI] | 457.3 | [435.2 467.8] | 462.2 | [448.3 475.0] | 0.63 |

FIG. 18

| Contrast | Region | Intra- | Inter- |
|---|---|---|---|
| Contrast | Inner Lumen | 98.0 ± 0.2 % | 96.5 ± 0.4 % |
| Contrast | Entire Aorta | 97.8 ± 0.5 % | 96.1 ± 0.6 % |
| Contrast | Outer Wall + ILT Only | 95.1 ± 0.8 % | 93.1 ± 0.9 % |
| Non-Contrast | Entire Aorta | 96.8 ± 0.4 % | 95.2 ± 0.8 % |

FIG. 20

| Region | Attention U-Net | 3D U-Net |
|---|---|---|
| Inner Lumen | 96.8 ± 0.2 % | 94.4 ± 0.4 % |
| Entire AAA | 94.8 ± 0.5 % | 89.5 ± 0.6 % |
| Outer Wall + ILT Only | 88.2 ± 0.8 % | 85.2 ± 0.9 % |

*FIG. 23*

| | U-Net A | U-Net B | U-Net C |
|---|---|---|---|
| Input Data | Low Resolution, Isotropic CTA | High Resolution, Isotropic CTA Region (Aortic Arch) | High Resolution, Isotropic CTA Region (Desc. Aorta/AAA) |
| Output Segmentation | Entire Aorta | Aortic Arch (Lumen, Outer Wall) | Desc. Aorta/AAA (Lumen, Outer Wall) |
| DICE(%) Combined | 93.4 ± 1.2 % | 95.8 ± 0.6 % | 94.8 ± 0.5 % |
| DICE(%) Inner Lumen | - | 96.3 ± 0.4 % | 96.8 ± 0.2 % |
| DICE(%) ILT/Outer Wall | - | 84.3 ± 1.2 % | 89.3 ± 0.5 % |

FIG. 25

| Input Data | Low Resolution, Isotropic Non-Contrast CT | High Resolution, Isotropic Non-Contrast CT (Desc. Aorta/AAA) |
|---|---|---|
| | U-Net D | U-Net E |
| Output Segmentation | Entire Aorta | Desc. Aorta/AAA (Lumen, Outer Wall) |
| DICE(%) Combined | 88.7 ± 0.5 % | 93.2 ± 0.7% |

COMPUTERISED TOMOGRAPHY IMAGE PROCESSING

CROSS-REFERENCE TO RELATED APPLICATIONS

This application is the National Stage of International Application No. PCT/GB2020/052014, filed Aug. 21, 2020, which claims priority to GB 1912150.8, filed Aug. 23, 2019, GB 2001792.7, filed Feb. 10, 2020, and GB 2001791.9, filed Feb. 10, 2020, which are entirely incorporated herein by reference.

TECHNICAL FIELD

The present disclosure relates to computerised tomography (CT) imaging. More particularly, the present disclosure relates to the use of machine learning algorithms in the processing of CT images.

BACKGROUND

A computerised tomography (CT) scan, sometimes referred to as a CAT scan, is a diagnostic imaging procedure which uses x-rays impinging on a subject, such as the human body, to produce cross-sectional images, sometimes called slices, of a targeted region of the subject. The CT images are usually captured at a range of angles about the subject. The cross-sectional slices are then collated to produce a detailed three-dimensional image of the targeted region of the subject, which can be used to diagnose conditions including damage to bones, injuries to internal organs, problems with blood flow, stroke, and cancer.

An abdominal aortic aneurysm (AAA) is an example of a condition that may be diagnosed using CT images obtained from a CT scan. AAA is a bulging, dilation, or ballooning in the wall of the abdominal aorta, caused due to weakness or degeneration that develops in a portion of the aorta. Due to the constant pressure on the walls of the abdominal aorta, the aneurysm enlarges, stretching the walls of the artery thinner, thereby compromising the artery wall's ability to stretch any further. At this point, the aneurysm is at risk of rupturing and causing potentially fatal bleeding, just as a balloon will pop when blown up too much. Images obtained from a CT scan can enable medical/surgical professionals to monitor the growth of the aneurysm in the patient and/or make plans for surgical repair of the aneurysm. Of course, CT scans are also beneficial in diagnosing and treating other conditions. In particular, CT angiograms are widely utilised in all fields of cardiovascular surgery/medicine.

In order to make blood vessels such as the aorta visible on a CT image, a radiocontrast agent (hereafter referred to as a contrast agent) can be introduced into the patient. As the radiodensity of blood and the surrounding tissue is similar it can be difficult for the human eye to distinguish the interface between blood vessels and the surrounding tissue on CT images obtained without a contrast agent. The introduction of a contrast agent helps distinguish or "contrast" selected areas of the body from the surrounding tissue.

There are numerous types of contrast agents, most of which are iodine based. Contrast agents have a chemical structure such that they limit the ability of x-rays to pass or reflect or refract x-rays. As the contrast material only fills the arterial (or venous) spaces to which blood travels, the radiodensity of the contrast agent in the blood vessels is different to that of the surrounding tissue. As a result, CT images obtained with a contrast agent help distinguish or "contrast" blood vessels and features of the blood vessels from the surrounding tissue.

In the case of an aortic aneurysm, the aorta often contains an intra-luminal thrombus within the aneurysm sac and full visualisation of the thrombus morphology, and its relation to the artery wall is important for monitoring the growth of the aneurysm and/or making plans for surgical repair of the aneurysm.

Current clinical guidelines for the management of AAA are based on criteria readily derived from the maximum diameter. The rationale behind the use of this singular parameter arises from the Young-Laplace equation, which states that wall tension in regular, symmetric and thin-walled spheres is directly proportional to their radii. Therefore, aneurysms larger than 5.5 cm and those with an expansion rate ≥1 cm/year are recommended for surgical intervention. Aneurysmal screening by measuring this parameter is a cost-effective modality to reduce the incidence of AAA rupture and is being increasingly adopted in many countries.

However, aneurysmal growth is a complex process that is poorly understood and requires significant exploration. AAAs are often asymmetric, tortuous, and the intra-luminal thrombus can have a varied thickness and density. Furthermore, AAA diameter is a crude unidimensional measurement of growth and in many instances remains constant despite significant changes in volume and morphology. This complicates the model assumed by the implementation of the Young-Laplace equation and illustrates the difficulty of individualizing surveillance protocols. Additionally, there is emerging evidence that geometric and volumetric measurements of AAA are patient-specific and more readily influence AAA growth. As small AAAs enlarge, a variety of geometrical changes have been observed to either promote rupture risk or growth deceleration. Isolating and deciphering these changes may allow a medical/surgical professional to predict AAA growth and progression in each patient.

In this instance, reconstruction of the aorta with the aneurysmal outer wall is a prerequisite for the extraction of many relevant parameters such as the diameter of an AAA or a blood vessel. Manual segmentation, although possible, is tedious, time-consuming and dependent on the training of the user. In addition, semi-automatic segmentation methods using open-source or existing commercially available software are limited to that of the inner aortic wall. This poses limitations on the analysis of data obtained from, for example, a AAA such as the inability to calculate the AAA volume which is a key factor in determining future growth rate of an aneurysm.

The present application addresses several of the problems described above.

SUMMARY

As used in the present specification and in the appended claims the term "contrast CT image" or "contrast-enhanced CT image" is understood to mean an x-ray image obtained from a CT scan performed on a subject with a contrast agent present within the subject during scanning. Often herein, the term "contrast CT image" and the term "contrast-enhanced CT image" are abbreviated to "CCT image". The term "non-contrast CT image" as used herein is understood to mean an x-ray image obtained from a CT scan performed on a subject in the absence of a contrast agent. Often herein, the term "non-contrast CT image" is abbreviated to "NCT image". In CT scans, the values of voxels are usually given in Hounsfield units, giving the opacity of material to x-rays.

According to an aspect of the invention, a method is disclosed for training a machine learning image segmentation algorithm to segment structural features of a blood vessel in a computed tomography (CT) image. The method comprises receiving a labelled training set for the machine learning image segmentation algorithm. The labelled training set comprises a plurality of CT images, each CT image of the plurality of CT images showing a targeted region of a subject, the targeted region including at least one blood vessel. The labelled training set further comprises a corresponding plurality of segmentation masks, each segmentation mask labelling at least one structural feature of a blood vessel in a corresponding CT image of the plurality of CT images. The method further comprises training a machine learning image segmentation algorithm, using the plurality of CT images and the corresponding plurality of segmentation masks, to learn features of the CT images that correspond to structural features of the blood vessels labelled by the segmentation masks, and output a trained image segmentation model. The method further comprises outputting the trained image segmentation model usable for segmenting structural features of a blood vessel in a CT image.

Traditionally, CT scans have been analysed by human specialists to identify structural features of a blood vessel shown in a contrast CT image. In what amounts to a very time-consuming process, human specialists have thus determined the locations and outlines of, for example, the different features of an aneurysm, including the outline of the inner lumen, thrombus, and outer wall. Advantageously, by providing a method as described herein for training a machine learning image segmentation algorithm, one may ultimately speed up the process of identifying/segmenting such structural features.

The term "targeted region" as used herein is understood to mean the region of a subject/patient on a CT image that is of medical/clinical interest to the medical practitioner/surgeon, for example a chest cavity, an abdominal cavity or any other region of interest. For example, in the case of a patient having an abdominal aortic aneurysm (AAA), the targeted region as used herein may be understood to mean a region of focus occupied by the abdominal aorta on the CT image. The targeted region may, of course, include more than one blood vessel.

The blood vessel may be any suitable blood vessel, for example a vein or an artery. For example, the at least one blood vessel of the targeted region of the CT image may include the aorta. For example, the at least one blood vessel of the targeted region of the CT image may include a renal artery. For example, the at least one blood vessel of the targeted region of the CT image may include a mesenteric artery. For example, the at least one blood vessel of the targeted region of the CT image may include an iliac artery.

Structural features may be understood to mean features of the blood vessel having a distinct intrinsic nature identifiable through image segmentation. For example, a structural feature may comprise an arterial or venous wall, an outer diameter or inner diameter of a blood vessel and so on. The structural features of at least one blood vessel may include for example the other wall or outer lumen and/or the inner lumen of the blood vessel. Structural features may be any anatomical or pathological features discernible from a CT scan (such as calcification, dissection flaps, false lumen, ulcers, atherosclerotic plaque, thrombus etc).

In some examples, the structural features may comprise structural features of an aneurysm, for example an aortic aneurysm. The structural features of the aortic aneurysm may include for example the thrombus, and lumen of the aorta, where the thrombus is predominantly fibrinous and collagenous, with red cells/platelets, whereas the lumen is predominantly filled with red blood cells. Structural features may include one or more boundaries for example. Structural features may include the outer lumen, intima, or media.

A subject may be understood to mean a human or animal or other suitable organism having blood vessels, or a sample therefrom.

In computer vision, image segmentation is the process of partitioning a digital image into multiple segments. A goal of segmentation is to simplify and/or change the representation of an image into something that is more meaningful and easier to analyse. Image segmentation is typically used to locate objects and boundaries (lines, curves, etc.) in images. More particularly, image segmentation is the process of assigning a label to pixels/voxels in an image such that pixels/voxels with the same label share certain characteristics or computed properties such as colour or intensity. A segmentation mask as used herein may be understood to mean such a labelling of features in the corresponding CT image from which it was generated. More particularly, a segmentation mask may be understood to mean a labelling of pixels/voxels in at least one region of a corresponding CT image, such that pixels/voxels with the same label share characteristics, and may be mappable back to features in the target region shown in the scan. For example, features of a blood vessel in a contrast CT image may be manually labelled or tagged in some way identifiable to a computer processor, or traditional image segmentation algorithms may be used to pick out the features of the blood vessel of interest. The data concerning the labelling or tagging may be referred to as a segmentation mask. Accordingly, the segmentation mask may be used as "ground truth" in the machine learning image segmentation algorithm. A segmentation mask may also be known as a pre-defined segmentation, segmentation data, a segmentation template, segmented contours, a labelled dataset, or a labelled segmentation. Each segmentation mask of the plurality of segmentation masks may comprise a binary segmentation mask, (e.g. in which each region is labelled as a "0" or a "1", or as foreground or background for example). A segmentation mask may not be binary. For example, a segmentation template may contain several labels to distinguish between several different regions. As an example, a segmentation template may include an RGB colouring or any other such labelling.

The term "labelled training set" as used herein is understood to mean the dataset obtained from a plurality of CT images of multiple patients or the same patient which is used to train a machine learning algorithm to label or otherwise identify the features of one or more blood vessels in a CT image. Except where otherwise stated, a CT image may comprise a CCT image or an NCT image. For example, a contrast CT scan or a non-contrast CT scan of a subject would ordinarily generate several CT images of that subject. In establishing the training set, one or more of such images for the patient may be used. Additionally, one or more CT images from at least one further patient may also be used. The training set may be established from CT scan data for many patients, with many CT images for each patient. The labelled training set may accordingly include an CCT image and a respective segmentation mask. The machine learning image segmentation algorithm may learn by receiving the CCT image as input and comparing the resultant output to the respective segmentation mask, and then adjusting internal weights and biases via a backpropagation algorithm.

The computed tomography (CT) image may comprise a contrast CT image (CCT). That is, the method may be for training a machine learning image segmentation algorithm to segment structural features of a blood vessel in a contrast computed tomography (CCT) image. The labelled training set may or may not have been established using as described herein.

The CT image may comprise a non-contrast CT image (NCT). That is, the method may be for training a machine learning image segmentation algorithm to segment structural features of a blood vessel in a non-contrast computed tomography (NCT) image. Each segmentation mask may have been generated from a corresponding contrast computed tomography (CCT) image, each CCT image corresponding to an NCT image of the plurality of NCT images and showing the features of the blood vessel in the targeted region of the corresponding NCT image.

A CT image may comprise a 2D CT image or a 3D CT image.

The method may further comprise generating the labelled training set. Generating the labelled training set may comprise performing a method as described herein for establishing a labelled training set.

The machine learning image segmentation algorithm may be any suitable machine learning image segmentation algorithm. For example, the machine learning image segmentation algorithm may comprise a neural network. For example, the machine learning image segmentation algorithm may comprise a convolutional neural network. The machine learning image segmentation algorithm may be trained by minimising a cost function involving the segmentation mask information ("ground truth") and the output of the final layer of the network. The cost function may comprise any suitable cost function such as a quadratic cost function, a cross-entropy cross function, a log-likelihood cost function. The minimisation may be performed for example by gradient descent, stochastic gradient descent or variations thereof, using backpropagation to adjust weights and biases within the neural network accordingly. Training may involve the use of further techniques known to the skilled person, such as regularization. Mini-batch sizes and numbers of epochs may be selected and fine-tuned during training. The neural network may comprise several layers of neurons (which may be, for example, perceptrons, sigmoid neurons, tan h neurons, or rectified linear units/rectified linear neurons), and may include one or more convolution layers, and may include one or more max-pool layers, and may include a soft-max layer.

A trained image segmentation model may accordingly be understood to include all information determined in training. For example, the trained image segmentation model may include the complete collection of weights and biases for neurons established during training and details of hyperparameters such as the learning rate and mini-batch size.

The trained segmentation model may be validated using metrics such as the Sørensen-Dice coefficient, also known as a DICE score, which is a statistic used to gauge the similarity of two samples. That is, one may validate the model by calculating a DICE score or some other metric for a known segmentation mask ("ground truth") and a segmentation mask output from the model.

According to an aspect of the invention, a computer-readable medium is described herein. The computer-readable medium has instructions stored thereon which, when executed by one or more processors, cause the one or more processors to implement a method for training a machine learning image segmentation algorithm as described herein. The computer-readable medium may comprise a non-transitory computer-readable medium. The computer-readable medium may comprise, for example, a USB stick, a hard drive, or some other memory unit.

According to an aspect of the invention, a computing apparatus is provided herein. The computing apparatus is suitable for training a machine learning image segmentation algorithm to identify structural features of a blood vessel in a computed tomography (CT) image. The apparatus comprises one or more memory units. The computing apparatus further comprises one or more processors configured to execute instructions stored in the one or more memory units to perform a method for training a machine learning image segmentation algorithm as described herein.

According to an aspect of the invention, a method is disclosed, the method for segmenting structural features of a blood vessel in a computed tomography (CT) image. The method comprises providing the CT image to a trained image segmentation model, the trained image segmentation model trained to learn features of CT images that correspond to structural features of blood vessels. The method further comprises segmenting, using the trained image segmentation model, at least one structural feature of a blood vessel in the provided CT image.

Segmenting the at least one structural feature of a blood vessel in the provided CT image may comprise generating segmentation data. The segmentation data/segmentation mask may be understood to mean the labelling of the CT image output from the method. That is, the segmentation mask/segmentation data/segmentation template comprises the labelling used to identify segments in the CT image. The segmentation mask may be output in suitable form, for example as a digital file that can be mapped by the user on to the CT image. Additionally or alternatively, the predicted segmentation mask may be provided in an adapted version of the CT image containing, for example, a colouring in or highlighting of a segmented region.

According to an aspect of the invention, a computer-readable medium is described herein. The computer-readable medium has stored thereon segmentation data generated using a method as described herein. The computer-readable medium may comprise a non-transitory computer-readable medium. The computer-readable medium may comprise, for example, a USB stick, a hard drive, or some other memory unit.

According to an aspect of the invention, a computer-readable medium is described herein. The computer-readable medium has stored thereon computer-readable code representative of the trained image segmentation model. The computer-readable medium may further have instructions stored thereon which, when executed by one or more processors, cause the one or more processors to implement a method as described herein to identify structural features of a blood vessel in a non-contrast computed tomography image. The computer-readable medium may comprise a non-transitory computer-readable medium. The computer-readable medium may comprise, for example, a USB stick, a hard drive, or some other memory unit.

According to an aspect of the invention, a computing apparatus is described herein. The computing apparatus is suitable for identifying structural features of a blood vessel in an unlabelled computed tomography image. The apparatus comprises one or more memory units. The apparatus further comprises one or more processors configured to execute instructions stored in the one or more memory units to perform a method as described herein to identify structural features of a blood vessel in a computed tomography image.

According to an aspect of the invention, a method is disclosed herein for establishing a labelled training set for training a machine learning image segmentation algorithm to segment structural features of a blood vessel in a contrast computed tomography (CCT) image. The method comprises receiving a plurality of CCT images, each CCT image showing a targeted region of a subject, the targeted region including at least one blood vessel. The method further comprises segmenting the plurality of CCT images to generate a corresponding plurality of segmentation masks, each segmentation mask labelling at least one structural feature of the at least one blood vessel in the corresponding CCT image. The labelled training set includes pairs of CCT images and the corresponding segmentation masks.

The phrase "receiving a plurality of contrast computed tomography (CCT) images" is understood to mean receiving data representative of one or more contrast CT scans. The data may be in any suitable format. The receiving may be performed, for example, by one or more processors of a computing apparatus (such as that shown in FIG. 5). The data may comprise information relating to the measured intensity of the x-rays which is used to reconstruct a contrast CT image using various known CT reconstruction techniques. For example, the data may represent pixel/voxel intensities.

The method may further comprise expanding the training set by applying transformations to the CCT images and corresponding segmentation masks (i.e. adjusting the sheer and/or divergence) in order to further diversify the training set and therefore to improve the ability of the machine learning image segmentation algorithm to learn. Throughout this specification, reference to a training set comprising CT images and segmentation masks may be understood also to refer to such digitally transformed/augmented expanded datasets.

According to an aspect of the invention, a computer-readable medium is provided. The computer-readable medium has instructions stored thereon which, when executed by one or more processors, cause the one or more processors to implement a method as described herein for establishing a training set. The computer-readable medium may comprise a non-transitory computer-readable medium. The computer-readable medium may comprise, for example, a USB stick, a hard drive, or some other memory unit.

According to an aspect of the invention, a computing apparatus is provided. The computing apparatus is suitable for establishing a labelled training set for training a machine learning image segmentation algorithm to identify structural features of a blood vessel in a contrast computed tomography (CCT) image for identifying/segmenting structural features of a blood vessel in an unlabelled contrast computed tomography (CCT) image. The apparatus comprises one or more memory units. The apparatus further comprises one or more processors configured to execute instructions stored in the one or more memory units to perform a method as described herein for establishing a training set.

According to an aspect of the invention, a method is described herein. The method comprises sending an unlabelled computed tomography (CT) image to a server, the CT image showing a targeted region of a subject including at least one blood vessel. The method further comprises receiving, from the server, segmentation data for the CT image, the segmentation data labelling structural features of the at least one blood vessel of the targeted region.

According to an aspect of the invention, a computing apparatus is provided for performing such a method. The method may comprise one or more memory units. The computing apparatus may further comprise one or more processors configured to execute instructions stored in the one or more memory units to perform such a method. The server may perform a method for identifying structural features of a blood vessel in an unlabelled contrast computed tomography (CCT) image as described herein. The server may be held by a third party.

The computer program and/or the code for performing such methods as described herein may be provided to an apparatus, such as a computer, on the computer readable medium or computer program product. The computer readable medium could be, for example, an electronic, magnetic, optical, electromagnetic, infrared, or semiconductor system, or a propagation medium for data transmission, for example for downloading the code over the Internet. Alternatively, the computer readable medium could take the form of a physical computer readable medium such as semiconductor or solid-state memory, magnetic tape, a removable computer diskette, a random-access memory (RAM), a read-only memory (ROM), a rigid magnetic disc, and an optical disk, such as a CD-ROM, CD-R/W or DVD.

Many modifications and other embodiments of the inventions set out herein will come to mind to a person skilled in the art to which these inventions pertain in light of the teachings presented herein. Therefore, it will be understood that the disclosure herein is not to be limited to the specific embodiments disclosed herein. Moreover, although the description provided herein provides example embodiments in the context of certain combinations of elements, steps and/or functions may be provided by alternative embodiments without departing from the scope of the invention.

BRIEF DESCRIPTION OF THE FIGURES

Embodiments of the invention will now be described by way of example only, with reference to the accompanying figures, in which:

FIG. 3A shows a contrast CT image of an abdominal aortic region;

FIGS. 3B-3D show image masks obtained from the contrast CT image shown in FIG. 3A;

FIG. 14 shows a table indicating how scans of various patients were allocated between training, validation and testing cohorts;

FIG. 16 shows a table describing all of the 3D U-Nets trained and evaluated as part of a study described herein;

FIG. 17 shows a table detailing image characteristics of the images within the training and external test cohorts in the study;

FIG. 18 shows a table indicating DICE score metrics for intra-/inter-operator aortic segmentations;

FIG. 20 shows a table of aortic segmentation accuracy;

FIG. 23 shows a table of DICE scores for aortic segmentation for attention-based U-Nets A-C;

FIG. 25 shows a table of DICE scores for aortic segmentation for attention-based U-Nets D and attention-based U-Net E;

Throughout the description and the drawings, like reference numerals refer to like parts.

DETAILED DESCRIPTION

The present disclosure provides ways of training a machine learning image segmentation algorithm to segment structural features of a blood vessel in a computed tomography (CT) image, and further discloses methods for establishing a training set used to train the machine learning image segmentation algorithm to segment structural features of a blood vessel in a CT image. Whilst various embodiments are described below, the invention is not limited to these embodiments, and variations of these embodiments may well fall within the scope of the invention which is to be limited only by the appended claims.

A computerised tomography (CT) scan uses computer-processed combinations of multiple X-ray measurements taken from different angles to produce cross-sectional images (virtual "slices") of specific areas of a scanned object. This allows visualisation inside the object without cutting it open. Since the invention of the first commercially available CT scanner in 1972, the use of CT scans for the diagnosis and management of disease is extensively embedded in every field of modern medicine. In the NHS alone, ~6 million CT scans were performed in 2018-2019.

Visualisation of blood vessels on a routine CT scan is challenging. Blood vessels consist of vessel wall structures, and the contents within the vessel lumen (blood, clot, plaques, etc). These components have similar radio-densities (measured in Hounsfield Unit, HU) to the adjacent soft tissue structures. Injection of intravenous contrast enhances the radio-density within vessel lumens and enables its reconstruction. The produced CT angiogram is routinely utilised to diagnose medical problems related to blood vessels.

CT angiograms are widely used in all fields of cardiovascular surgery/medicine. When treatment of an artery, for example the aorta, is being considered, a medical/surgical professional usually requires a detailed view of the artery to differentiate the morphology/anatomy of the arterial structures. In the case of abdominal aortic aneurysms (AAAs), there is usually luminal thrombus within the aneurysm sac and full visualisation of the thrombus morphology, and its relation to the artery wall, is important for planning surgical intervention, for example by stenting or open repair.

Pathological changes can be present in the blood lumen, vessel wall or a combination of both.

Figure 1B:
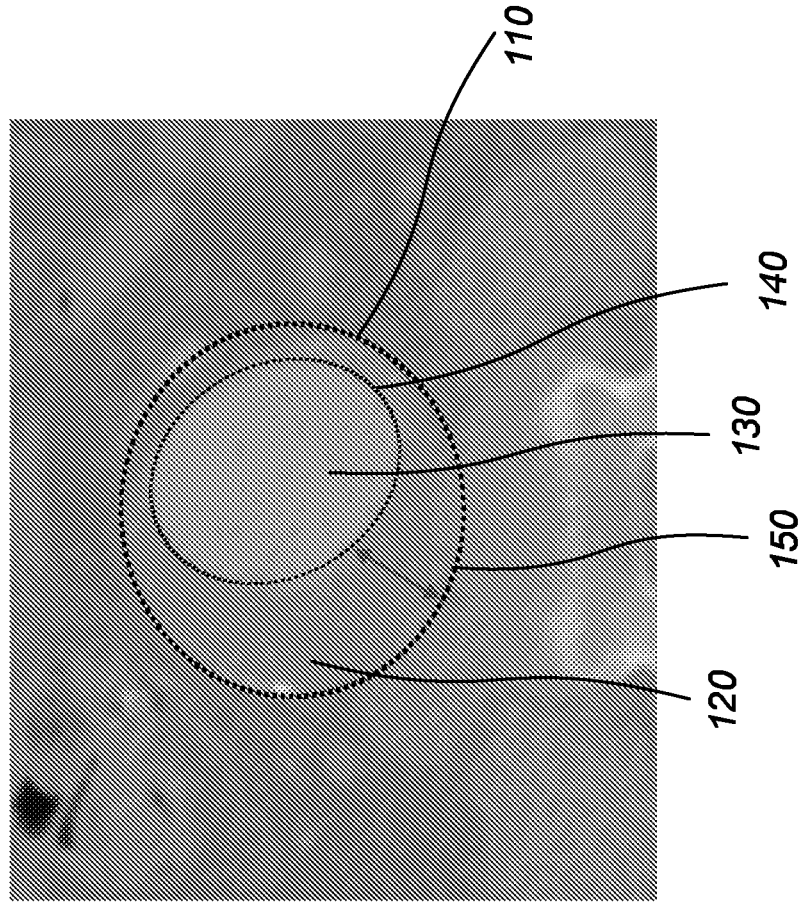
FIG. 1B shows a contrast CT image of an abdominal aortic region.
Figure 1A:
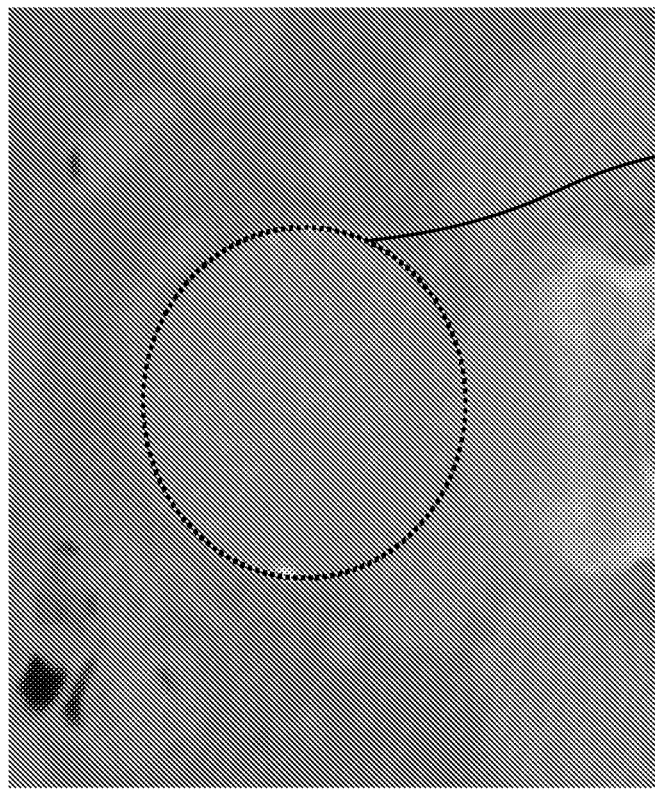
FIG. 1A shows a non-contrast CT image of an abdominal aortic region.

FIGS. 1A and 1B show axial slices of an abdominal aortic region obtained from a non-contrast CT scan and a contrast CT scan respectively. The aneurysm lies within region 110 of FIGS. 1A and 1B. As described above, to enable a surgeon or other medical professional to monitor the growth of the aneurysm and/or plan for surgery, full visualisation of the thrombus morphology, and its relation to the artery wall is important. The CCT image of FIG. 1B clearly shows the interface between the aortic inner lumen 130, and the intra-luminal thrombus (ILT) 120, where the thickness (double-headed arrow) of the ILT is defined as the distance from the outer aneurysmal wall 150 to the inner aortic lumen wall 140. These structural features 120 and 130 of the targeted region 110 are very difficult to distinguish in the NCT image with the naked eye, as is apparent from viewing FIG. 1A.

Figure 2:
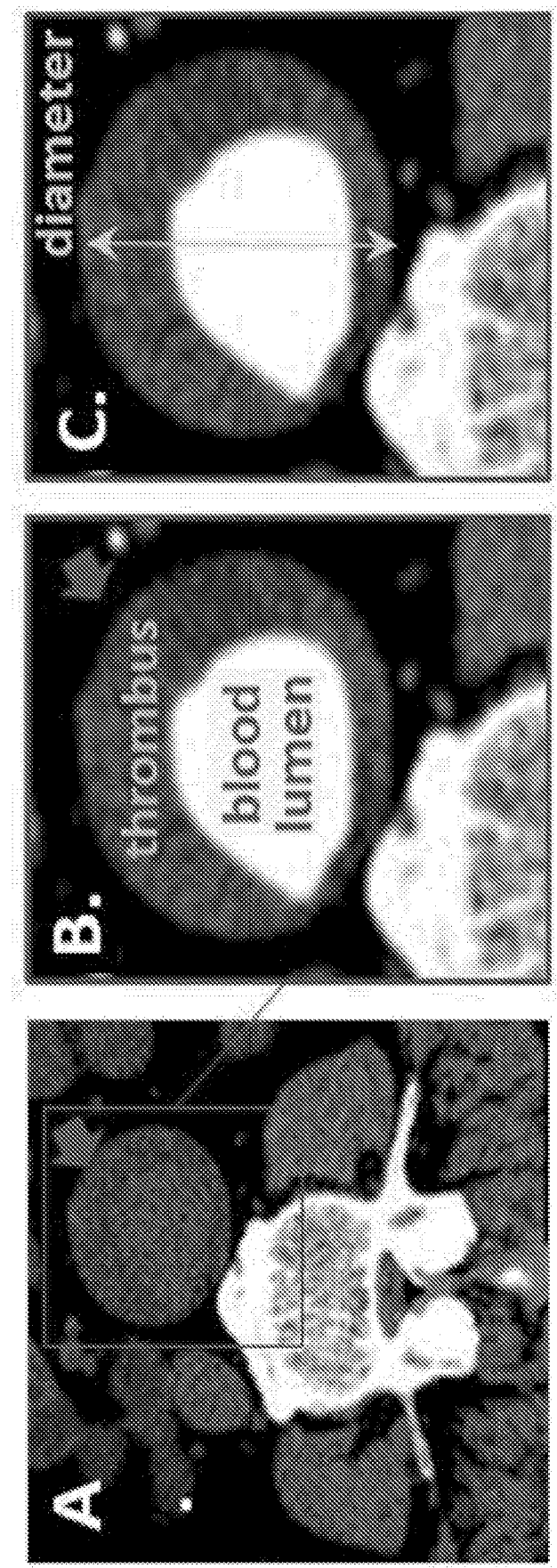
FIG. 2 shows a non-contrast CT scan image and two contrast CT scan images with some structural features labelled.

FIG. 2 shows further axial slices taken from a non-contrast computed tomography (NCT) scan and a contrast-enhanced CT scan (CCT). In particular, panel A (left-hand panel of FIG. 2) shows an NCT axial slice. Panels B and C (middle and right-hand panels of FIG. 2 respectively) show contrast images of the region shown in the box in panel A. In the example of aortic aneurysms (panel A, indicated by the arrow), there is usually a blood clot or thrombus adherent to the aortic wall within the aneurysm sac (panel B, red arrow points toward the aortic aneurysm). In Panel B, the lumen and thrombus are indicated. In Panel C, the diameter of the aneurysm is indicated. As explained above, the diameter of the aneurysm is important for the clinical care and research of patients with abdominal aortic aneurysms. Existing automated methods to reconstruct the angiogram would isolate the inner lumen but are unable to extract the thrombus and the complex thrombus-lumen interface. As such, there is no automated method to assess the aneurysm diameter (FIG. 1C) or thrombus volume.

As described above, semi-automatic segmentation methods using open-source software are limited to the segmentation of the aorta with the inner aortic wall 140, and segmentation of the aorta including the outer aneurysmal wall 140 is done manually. FIGS. 3A-3D and FIG. 4 below describe an example of manual segmentation of the structural features 130 and 120 of an abdominal aortic CCT scan.

FIG. 3A shows an axial slice of an abdominal aortic region obtained from a CCT scan of a patient, and corresponding image masks, FIG. 3B-3D, obtained from the CCT scan shown in FIG. 3A. The image masks shown in FIGS. 3B-3D are generated by manually segmenting the structural features 320 and 330 from the targeted region 310 of the CCT image based on an analysis of the Hounsfield units of the voxels in the CCT image. FIG. 3B shows the segmentation of the aortic inner lumen 330 from the targeted region 310. FIG. 3C shows the segmentation of both the aortic inner lumen 330 and the thrombus 320 from the targeted region 310. FIG. 3D shows the segmentation of solely the thrombus 320, which is obtained by subtracting the inner aortic mask, shown in FIG. 3B, from the inner aortic and thrombus mask, shown in FIG. 3C.

Figure 4B:
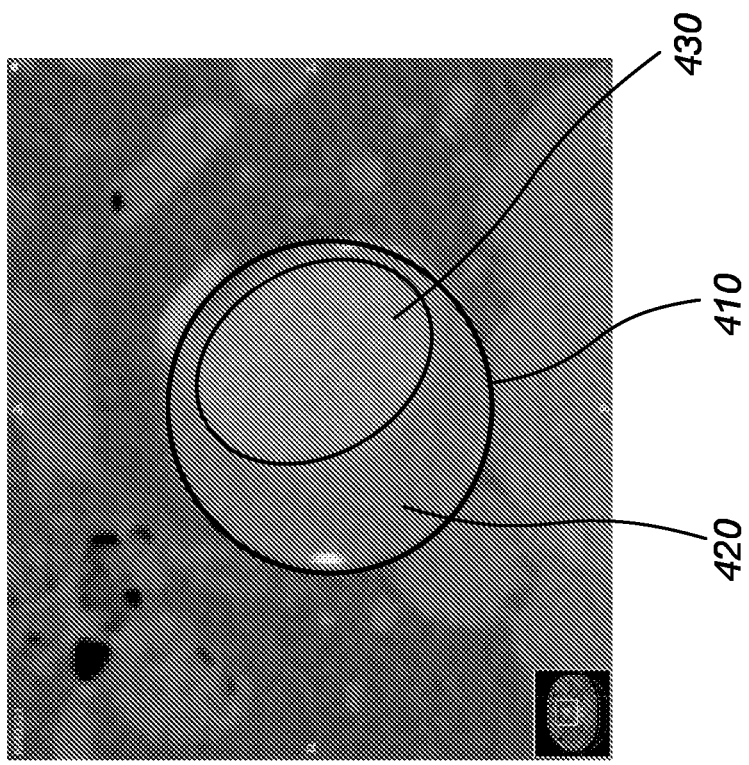
FIG. 4B shows a contrast CT image of an abdominal aortic region mapped with a mask demarcating structural features of the abdominal aorta.
Figure 4A:
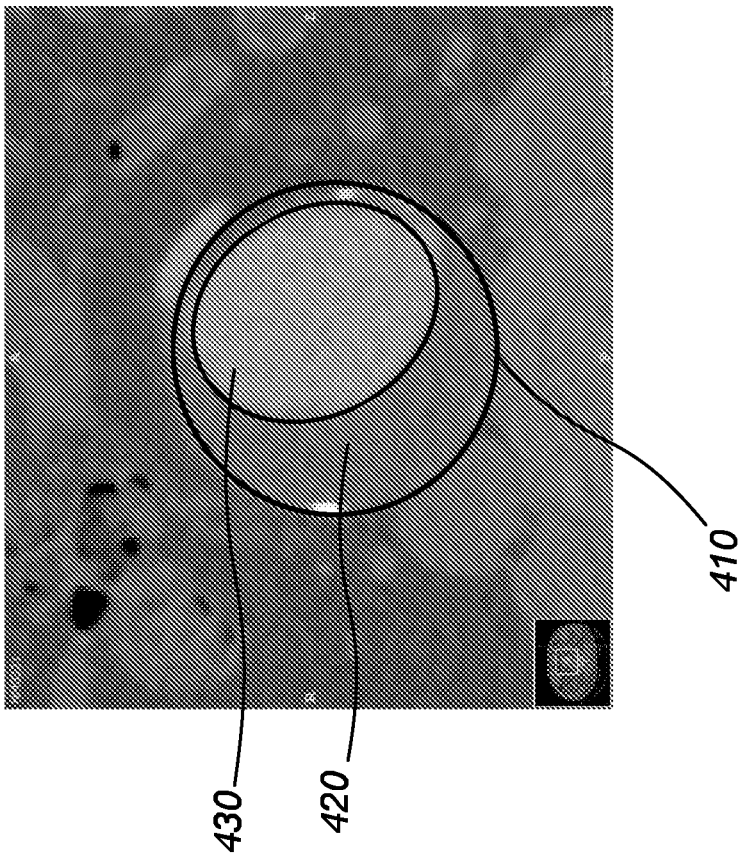
FIG. 4A shows a contrast CT image of an abdominal aortic region.

FIGS. 4A and 4B show axial slices of an abdominal aortic region of a patient obtained from a CCT scan. FIG. 4B shows overlying manually derived segmentation masks, where the segmentation masks demarcate the boundary between structural features of the targeted region 410. The demarcated regions display the thrombus 420, and the inner aortic lumen 430.

The inventors have developed a method for establishing a training set, as described below in relation to FIG. 5, to train a machine learning segmentation algorithm to segment structural features, such as the intra-luminal thrombus 120, of a blood vessel. This mitigates the need for manual segmentation of structural features of a blood vessel and in the case of an aneurysmal region such as a AAA allows for the volume of the aneurysm to be calculated.

A method for establishing a labelled training set for training a machine learning image segmentation algorithm to segment structural features of a blood vessel in a CT image will now be described in relation to the flowchart shown in FIG. 5. The method may be performed by any suitable computing apparatus, such as the computing apparatus 600 described in relation to FIG. 6 below.

At 510, the method comprises receiving a plurality of CCT images, each CCT image showing a targeted region of a subject, such as the targeted region 110 shown in FIG. 1A where the targeted region comprises an aortic aneurysm.

At 520, the method comprises segmenting the plurality of CCT images to generate a corresponding plurality of segmentation masks, where each segmentation mask labels at least one structural feature of the at least one blood vessel of the targeted region in the corresponding CCT image.

At 530, a labelled training set is established, wherein the labelled training set includes pairs of CCT images and the corresponding segmentation masks.

Figure 5:
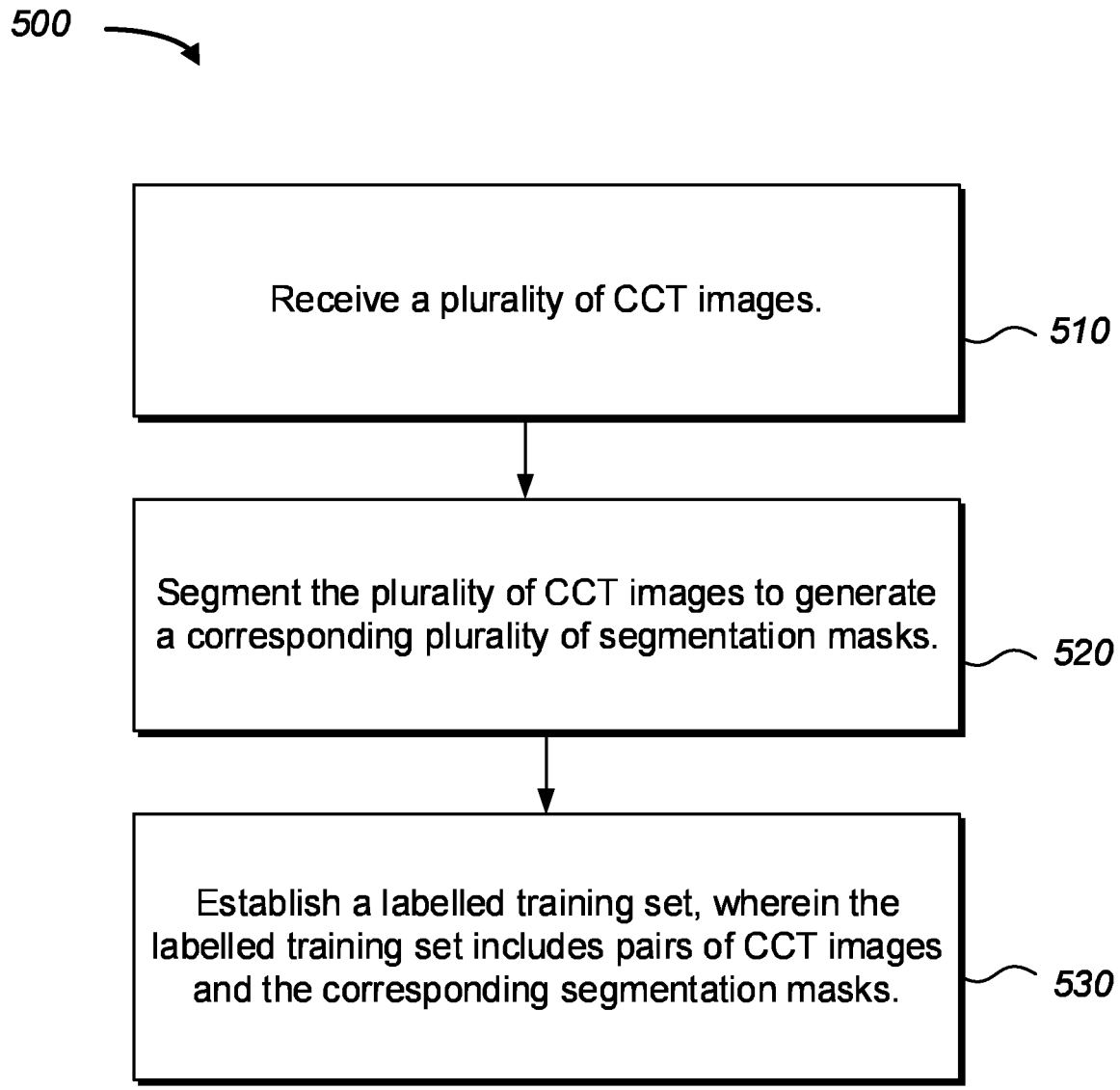
FIG. 5 shows a flowchart.
Figure 6:
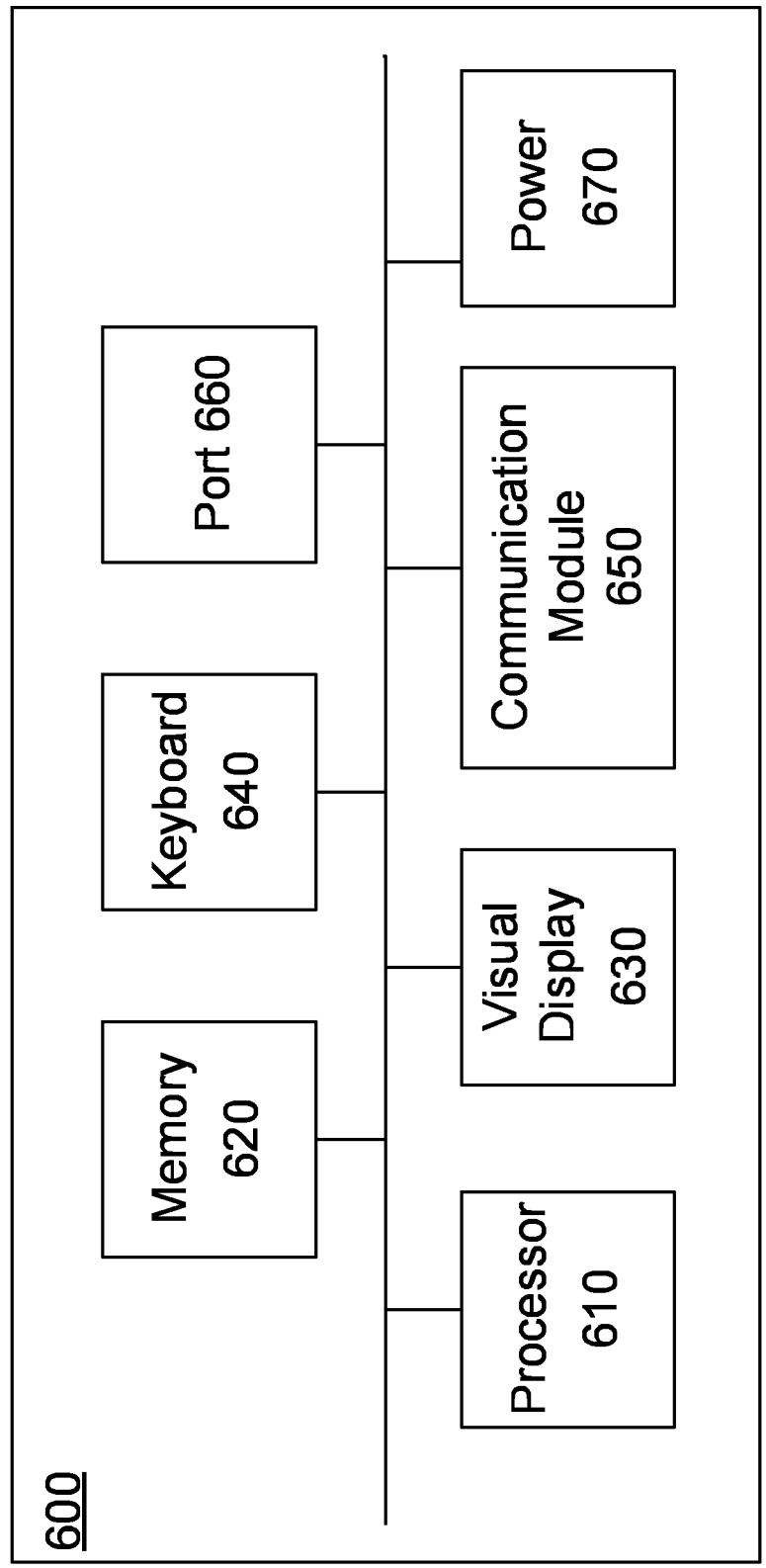
FIG. 6 shows a block diagram of a computing apparatus.

The method for establishing a labelled training set used to train a machine learning image segmentation algorithm, as described in FIG. 5, is suitable for performance by a computing apparatus such as computing apparatus 600 as shown in FIG. 6 and described below.

Computing apparatus 600 may comprise a computing device, a server, a mobile or portable computer and so on. Computing apparatus 600 may be distributed across multiple connected devices. Other architectures to that shown in FIG. 6 may be used as will be appreciated by the skilled person.

Referring to FIG. 6, computing apparatus 600 includes one or more processors 610, one or more memories 620, a number of optional user interfaces such as visual display 630 and virtual or physical keyboard 640, a communications module 650, and optionally a port 660 and optionally a power source 670. Each of components 610, 620, 630, 640, 650, 660, and 670 are interconnected using various busses. Processor 610 can process instructions for execution within the computing apparatus 600, including instructions stored in memory 620, received via communications module 650, or via port 660.

Memory 620 is for storing data within computing apparatus 600. The one or more memories 620 may include a volatile memory unit or units. The one or more memories may include a non-volatile memory unit or units. The one or more memories 620 may also be another form of computer-readable medium, such as a magnetic or optical disk. One or more memories 620 may provide mass storage for the computing apparatus 600. Instructions for performing a method as described herein may be stored within the one or more memories 620.

The communications module 650 is suitable for sending and receiving communications between processor 610 and remote systems.

The port 660 is suitable for receiving, for example, a non-transitory computer readable medium containing one or more instructions to be processed by the processor 610.

The processor 610 is configured to receive data, access the memory 620, and to act upon instructions received either from said memory 620 or a computer-readable storage medium connected to port 660, from communications module 650 or from user input device 640.

The computing apparatus 600 may receive, via the communications module 650, data representative of a plurality of contrast CT scans of a targeted region of a subject. The data received via the communications module 650 relating to a contrast CT scan may comprise information relating to the measured intensity of the x-rays impinging the targeted region of the subject. The processor 610 may be configured to follow instructions stored in one or more memories 620 to use the received data to reconstruct the corresponding contrast CT image using various CT reconstruction techniques.

The processor 610 may be configured to follow further instructions stored in the memory 620 to segment the plurality of CCT images to generate a corresponding plurality of segmentation masks, each segmentation mask labelling at least one structural feature of the at least one blood vessel of the targeted region in the corresponding CCT image. The reconstructed CCT image comprises voxels/pixels, and the generated plurality of segmentation masks may be binary segmentation masks, where the voxels/pixels comprising structural feature of the blood vessel of the targeted region may be labelled with a 1 and the voxels/pixels comprising features in the image which are not structural features of the blood vessel may be labelled with a 0 (for example).

The processor 610 may be configured to follow instructions stored in the memory 620 to pair a generated segmentation mask with a corresponding CCT image.

Based on the above description, computing apparatus 600 can be used to establish a labelled training set for training a machine learning image segmentation algorithm, where the established labelled training set includes information relating to pairings of CCT images and their corresponding segmentation masks. The skilled person would appreciate that other architectures to that shown in FIG. 6 may be used.

Figure 7:
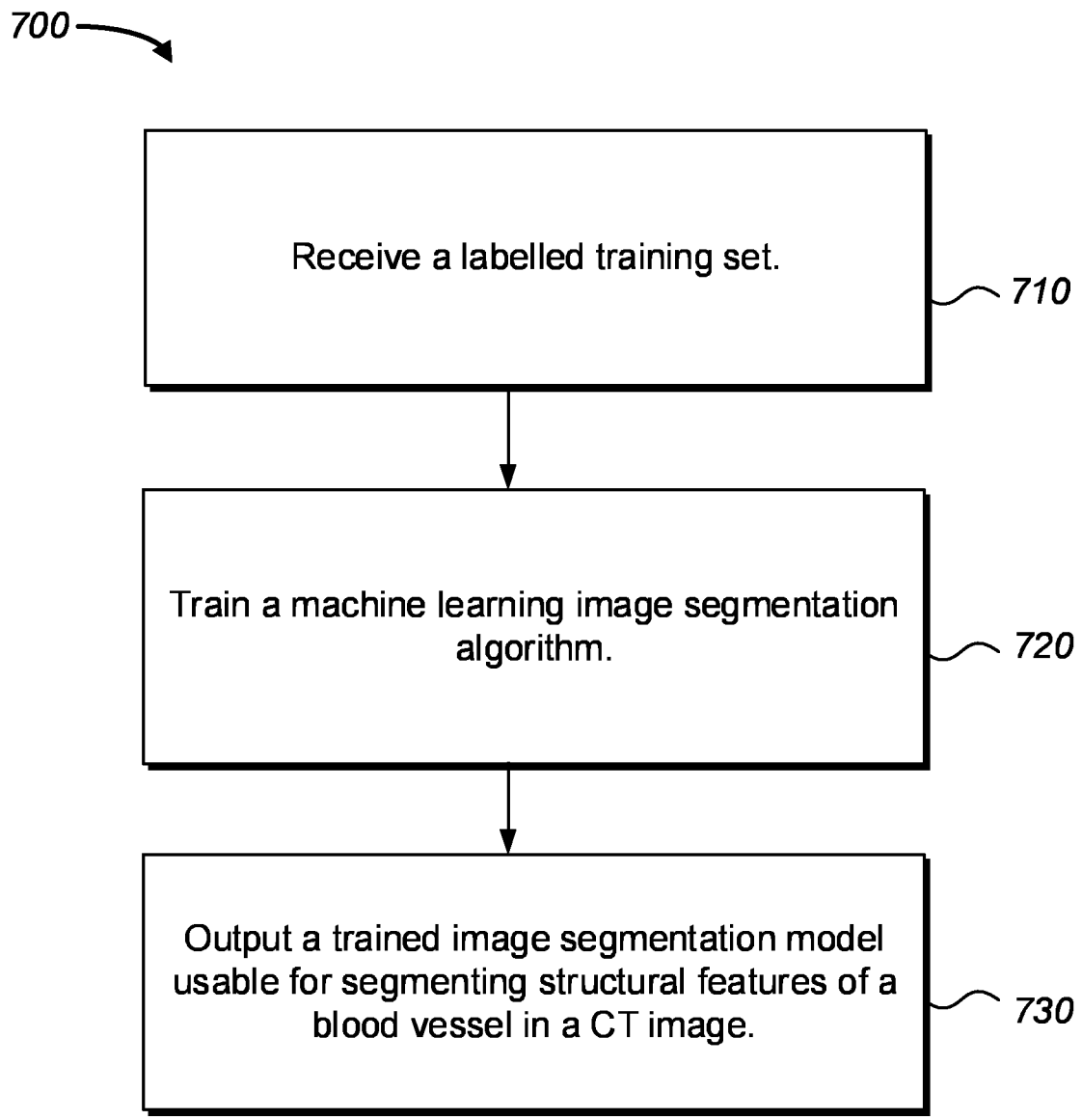
FIG. 7 shows a flowchart.

FIG. 7 shows a flowchart of a method for training a machine learning image segmentation algorithm to segment structural features of a blood vessel in a CT image. The method uses a training set, which may be a training set such as that described above in relation to FIG. 5. However, the skilled person would appreciate that the method may be used with NCT images provided an adequate training set is used.

At step 710, the method comprises receiving a labelled training set. The labelled training set comprises information relating to a plurality of CT images, where each CT image of the plurality of CT images shows a targeted region of a subject which includes at least one blood vessel. The training set further comprises a corresponding plurality of segmentation masks, where the segmentation masks are generated from a CT image and each segmentation mask labels at least one structural feature of a blood vessel in a corresponding CT image of the plurality of CT images.

At step 720, the method comprises training a machine learning segmentation algorithm using the plurality of CT images and the corresponding plurality of segmentation masks, to learn features of the CT images that correspond to structural features of the blood vessels labelled in the segmentation masks.

At step 730, the method comprises output of a trained image segmentation model usable for segmenting structural features of a blood vessel in a CT image.

The method for training a machine learning image segmentation algorithm, as described above in relation to FIG. 7, is suitable for performance by a computing apparatus such as computing apparatus 600 as shown in FIG. 6.

Figure 8:
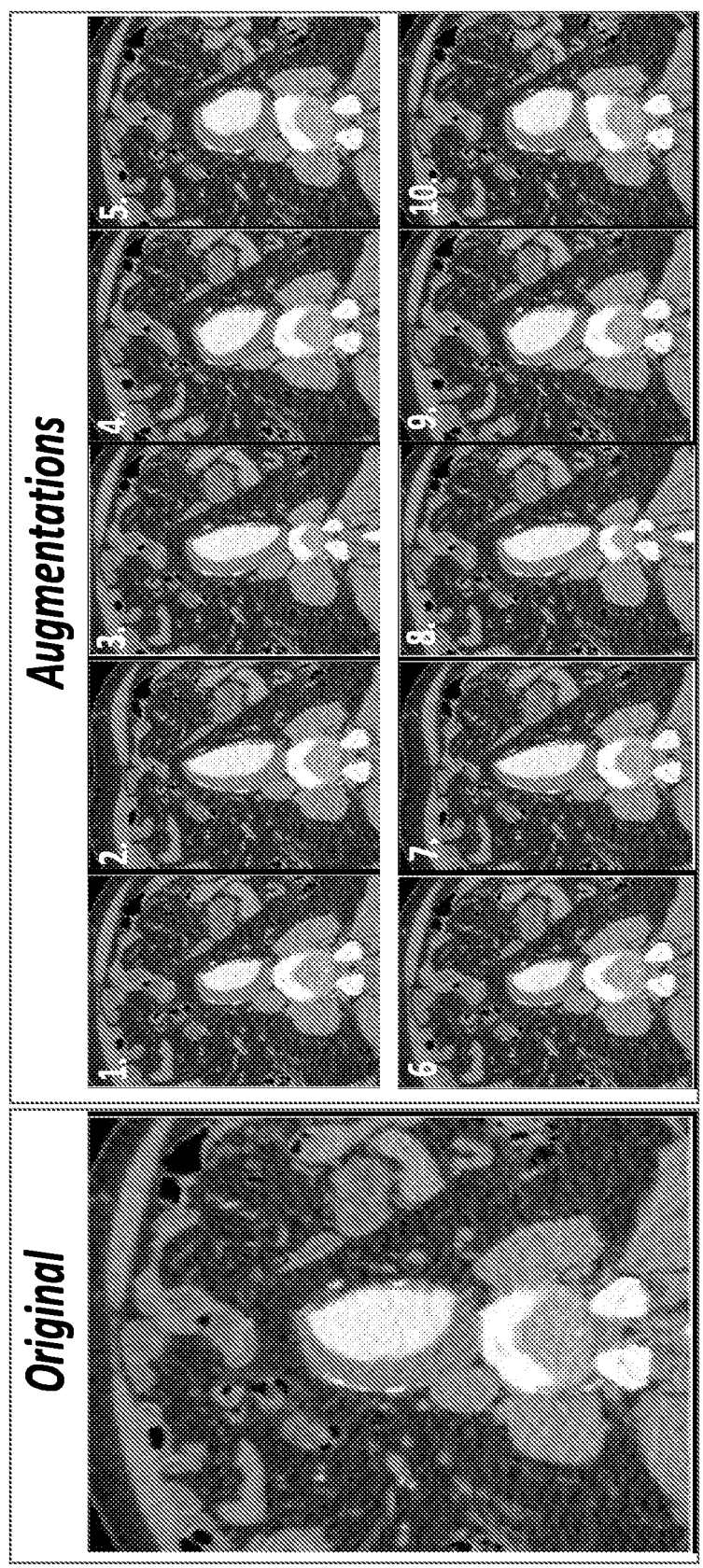
FIG. 8 shows a contrast axial CT slice with its associated augmentations.

The processor 610 may be configured to train a machine learning image segmentation algorithm to learn the features of CT images that correspond to structural features of blood vessels of the targeted region using the plurality of CT images and the corresponding plurality of segmentation masks. For each CT image and the corresponding segmentation mask, the processor 610 may follow instructions stored in one or more memories 620 to compare the segmentation mask with the corresponding CT image and adjust the internal weights of the image segmentation algorithm via backpropagation. Several iterations of the comparison between the CT image and the corresponding segmentation mask may be performed for each CT image from the plurality of CT images and the corresponding segmentation masks until a substantially optimized setting for the internal weights is achieved. The processor 610 may follow further instructions stored in one or more memories 620 to perform image transformations at each iteration for each CT image of the plurality of CT images to diversify the input data set and maximise learning. FIG. 8 below shows a single axial slice augmented ten times to diversify the training data set and maximize learning. The labelled training set may comprise such augmented images and corresponding (augmented) masks.

The processor 610 may be configured to follow further instructions to output the trained image segmentation model and store the trained image segmentation model in one or more memories 620. The trained image segmentation model may comprise for example the weights and biases established during training, along with any selected hyperparameters such as minibatch size or learning rate.

Figure 9:
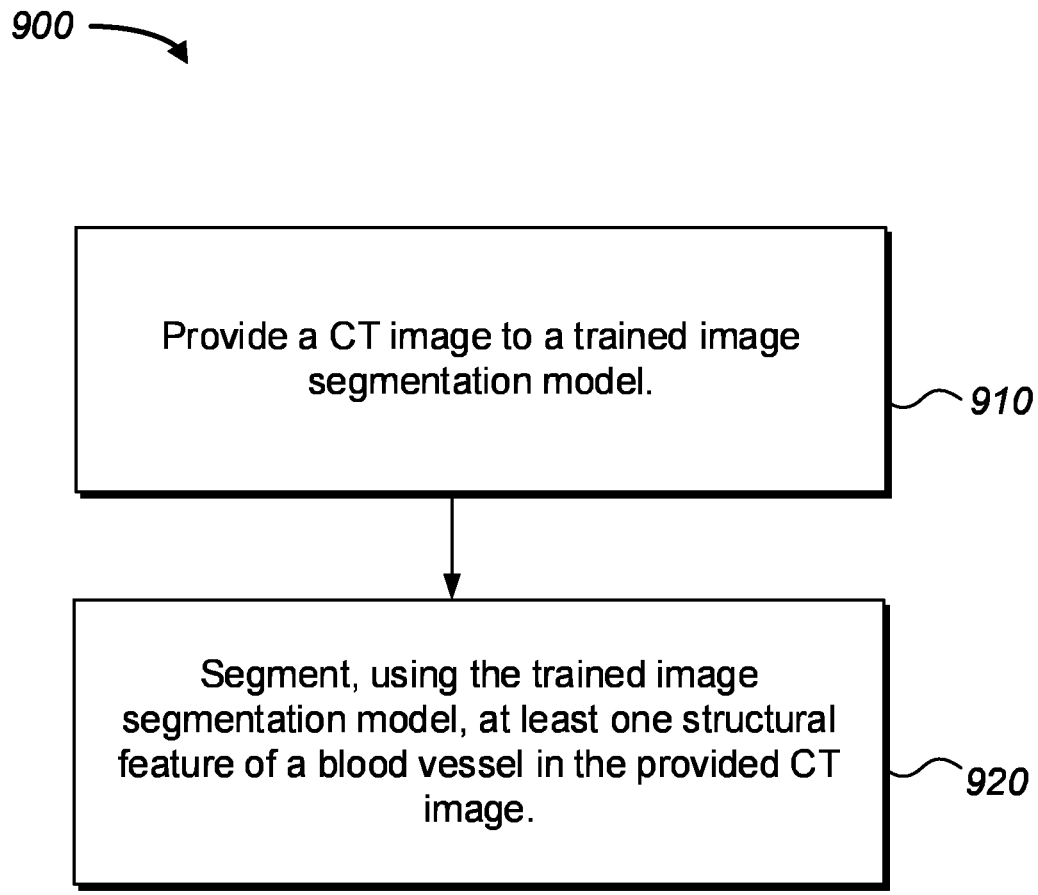
FIG. 9 shows a flowchart.

FIG. 9 shows a flowchart of a method for segmenting structural features of a blood vessel in a CT image.

At step 910, the method comprises providing the CT image to a trained image segmentation model which may be trained according to the method described above in relation to FIG. 7. The trained image segmentation model is trained to learn features of CT images that correspond to structural features such as the inner aortic lumen or in the case of an aortic aneurysm the trained image segmentation model is trained to learn features of a CT image that correspond to structural features such as the thrombus 120, inner aortic lumen 130 and outer aneurysmal wall 150.

At step 920, the method comprises segmenting, using the trained image segmentation model, at least one structural feature of a blood vessel in the provided CT image.

The method for segmenting structural features of a blood vessel in a CT image, as described above in relation to FIG. 9, is suitable for performance by a computing apparatus such as computing apparatus 600 as shown in FIG. 6.

The computing apparatus 600 may receive, via the communications module 650, data from a CT scan of a subject. The received data may comprise information relating to the measured intensity of the x-rays impinging the targeted region of the subject, for example pixel/voxel intensity.

The computing apparatus 600 may store a trained image segmentation model in one or more memories 620 of the computing apparatus 600, where the trained image segmentation model is trained to learn features of CT images that correspond to structural features of blood vessels of a targeted region. The processor 610 may be configured to input the received data from the CT scan to the trained image segmentation model.

The processor 610 may follow further instructions stored in memory 620 of the computing apparatus 600 to generate, using the trained image segmentation model, to segment at least one structural feature of a blood vessel in the provided CT image.

The inventors sought to use a modified version of a U-Net with attention gating and deep supervision to predict the inner lumen and outer wall from a given CT scan. The model was trained and tested over multiple iterations to achieve a particular task, in this case to extract the entirety of an aorta from the aortic root to the iliac bifurcation and automatically differentiate the outer aneurysmal wall 150 from the inner aortic lumen 130.

Figure 10:
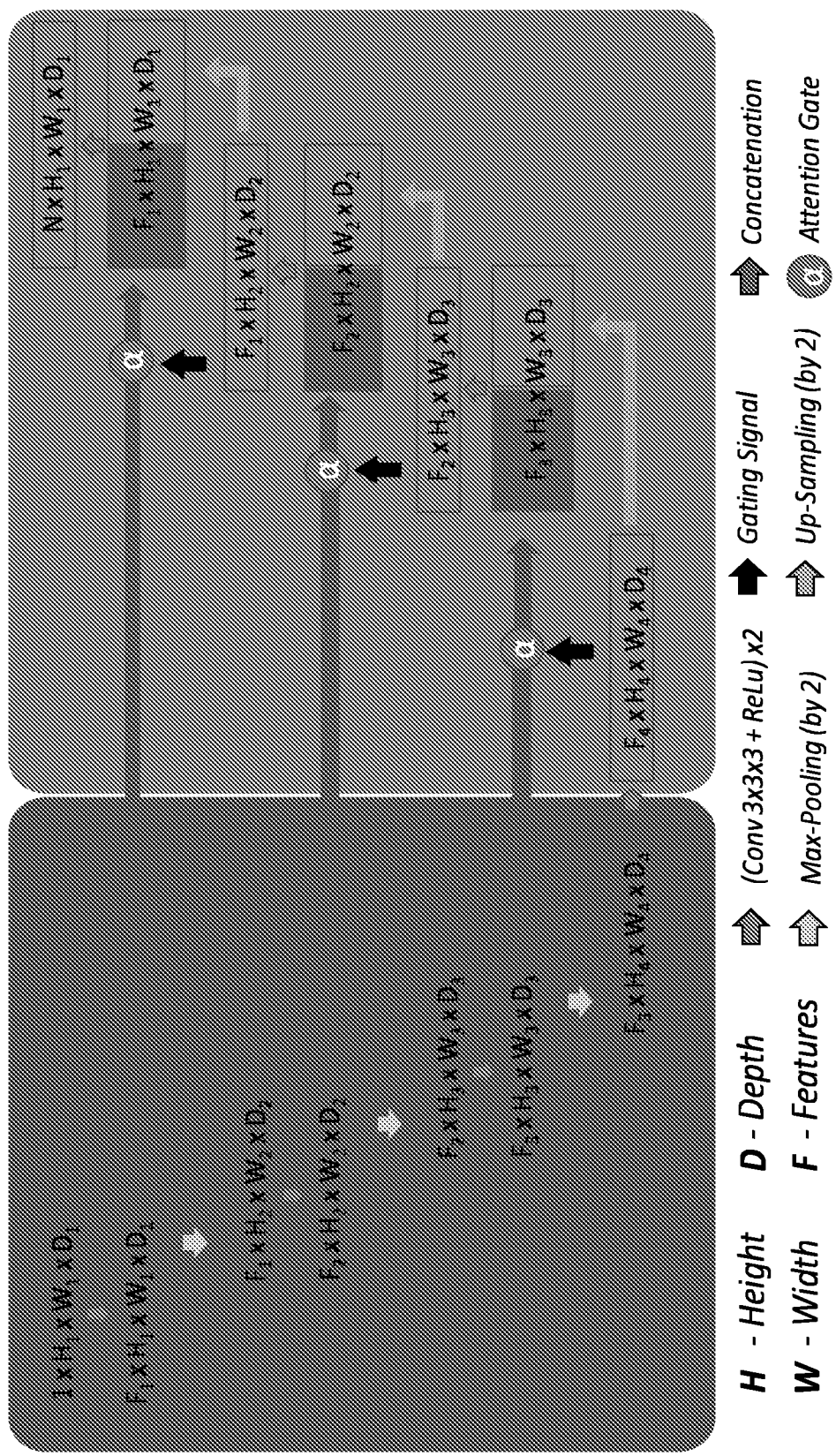
FIG. 10 illustrates a modified 3D U-Net architecture with attention gating.

The machine learning image segmentation architecture used in this experiment is shown in FIG. 10. The algorithm utilises deep learning and is based on a modified 3D U-Net architecture. U-NET is very good for biomedical image segmentation tasks. The general U-Net architecture used for the experiment comprises two components: a downsampling/contraction path (as shown on the left in FIG. 10) and an upsampling/expanding path (as shown on the right in FIG. 10). The contraction path serves to extract information and capture the context of the image at the expense of losing spatial information. This is achieved through a series of algebraic manipulations (convolutions and max-pooling/averaging) as shown in FIG. 10. During this process, the size of the input image is gradually reduced. In particular, in this example, the input image is of size 512×512×Z pixels where Z is the number of axial slices. The image is then sectioned into patches of size 160×160×96 and analysed. With each step for the downsampling path, the size of the input image is decreased by a factor of two. Accordingly, the downsampling path results in a resolution of 64×64×Z/4. This is followed by an expansion path, where the size of the image gradually increases and a predictive binary segmentation mask is output. This is accomplished using similar algebraic methods. The lost spatial information is restored using skip connections that connect the output of the down-sampling path with the feature maps/input of the up-sampling path at the same level. After each skip connection, two consecutive convolutions are used to integrate the spatial and contextual information to assemble a more precise output.

Attention gating is also used to train the machine learning image segmentation model to suppress irrelevant regions in an input image and to better highlight regions of interest.

Attention gates are used to focus on target structures without the need for additional training/supervision. The attention gates filter along both the forward and backward directions. Gradients originating from the background regions are down-weighted during the backward pass allowing model parameters to be updated mostly based on spatial regions relevant to the given task. Accordingly, the attention gates reduce the need for hard attention/external organ localisation (region-of-interest) models in image segmentation frameworks.

Deep supervision is also used to ensure the feature maps are semantically distinctive at each image scale. This helps to ensure that the attention gates across different scales and not predictions from a small subset are more likely to influence foreground content.

Each axial CT slice and their respective image masks/segmentation masks were augmented through image transformations (shear, divergence) to diversify the input data set and maximize learning. The initial learning rate and weight decay were set to $1.0 \times 10^{-4}$ and $1.0 \times 10^{-6}$, respectively. Training consisted of a total of 700 epochs with a batch size of 2 3D Images. Of the 143 images available, the training, validation and testing datasets consisted of 137, 3 and 3 images, respectively.

Figure 11:
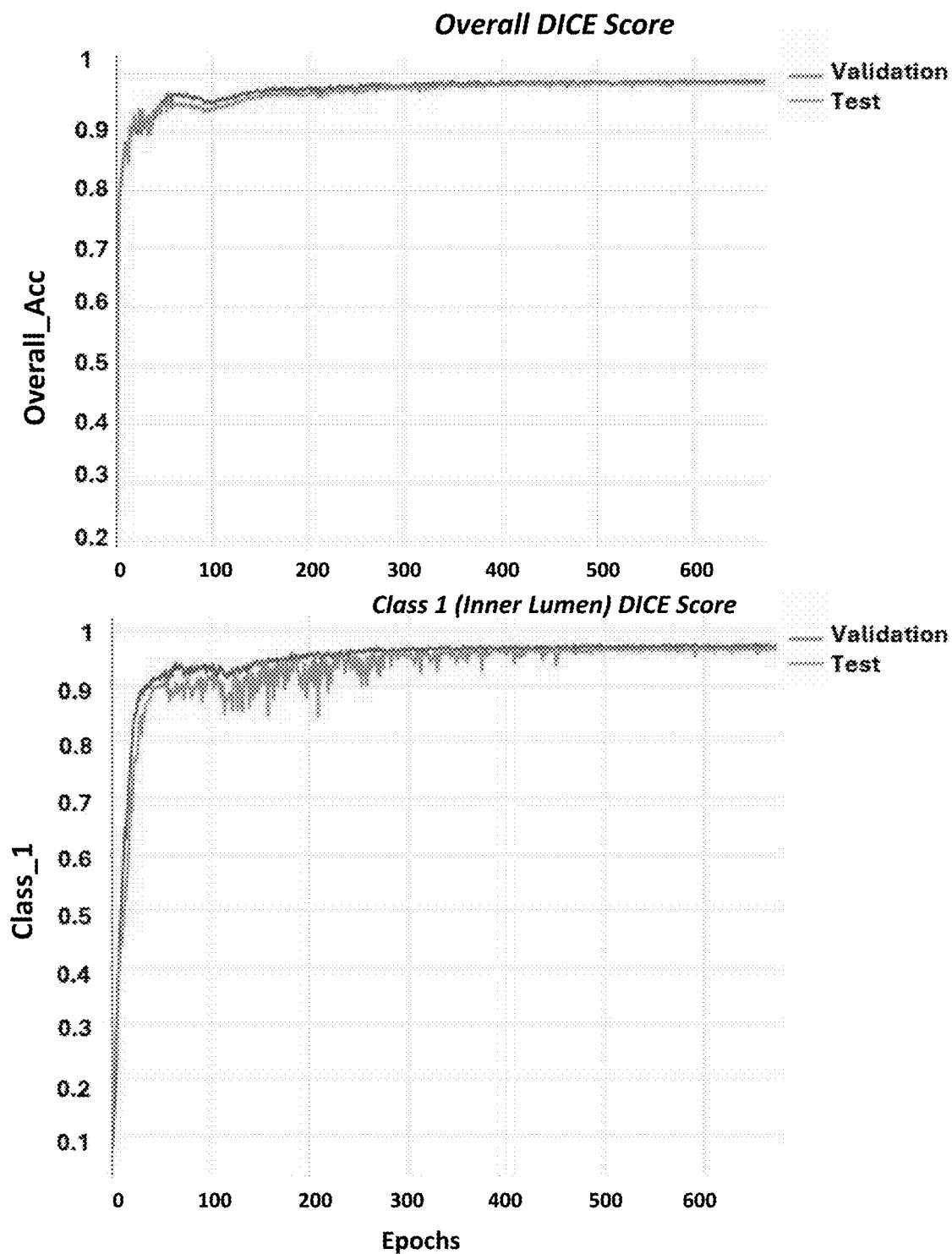
FIG. 11 shows graphs demonstrating the output of the machine learning image segmentation algorithm as applied to validation data and test data.
Figure 11:
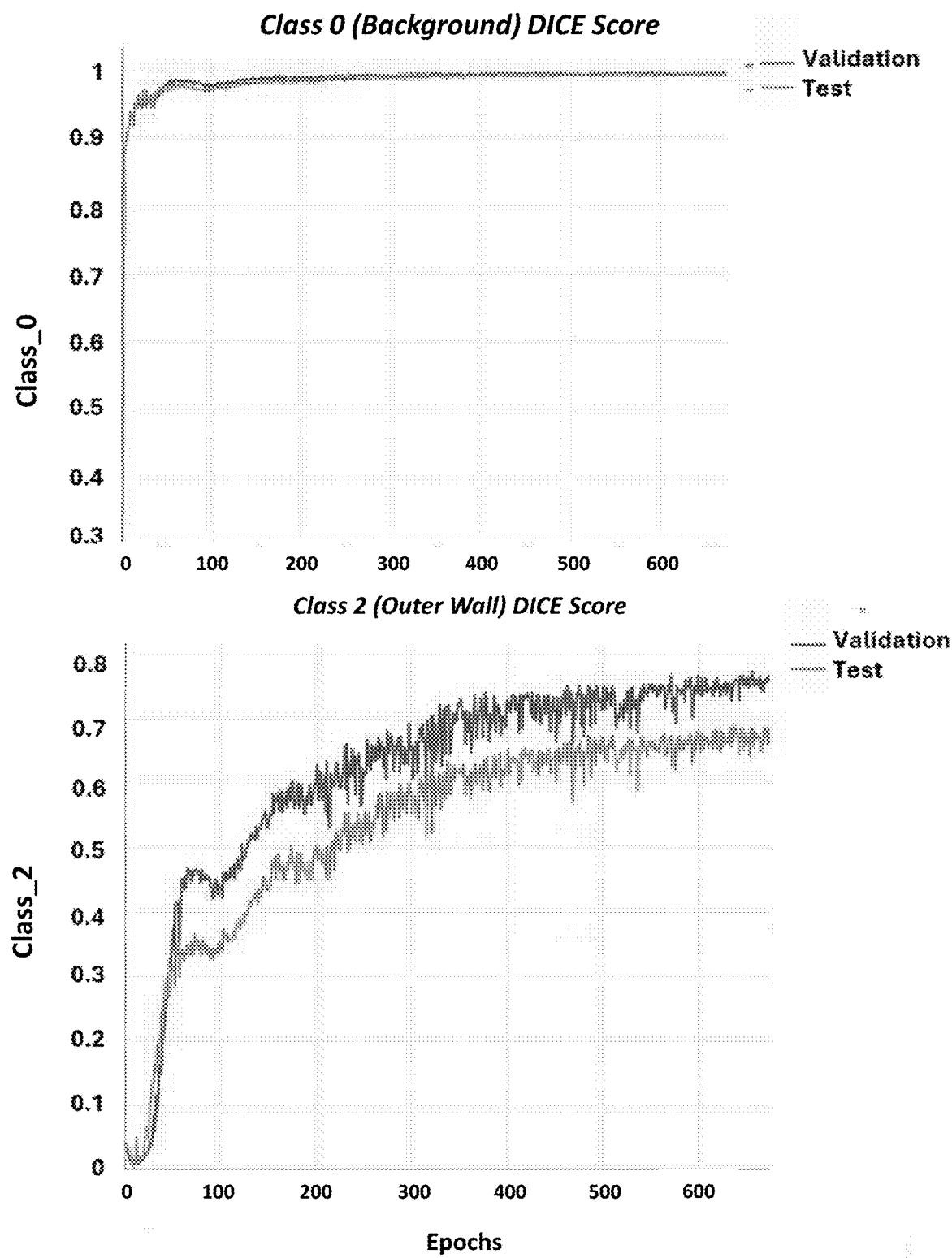

FIG. 11 shows several graphs demonstrating the improvement in accuracy as training progressed across the epochs. In particular, the top left image shows the overall accuracy, as calculated using the DICE score metric, for the validation data (blue) and test data (orange) of the model as the epochs progress to 700. The overall DICE score metrics reflects the similarity of the inner mask prediction to the ground truth inner mask, and as can be seen in the top left graph of FIG. 11, increased from 22.1% to approximately 98% for the test data set.

The top right graph in FIG. 11 shows the ability of the model to pick out the background in the validation (blue) and test (orange) images. Once again, the DICE score improved greatly with the number of epochs.

The bottom left graph in FIG. 11 demonstrates the ability of the model to pick out the inner lumen in the validation (blue) and test (orange) images. The bottom right graph in FIG. 11 demonstrates the ability of the model to pick out the outer wall in the validation (blue) and test (orange) images. Within the first 100 epochs the ability of this model to identify the inner lumen increased from 7.1% to 95%. For the remaining 600 epochs, this percentage increased to ~98% and plateaued. On the other hand, within the first 100 epochs, the ability of the model to identify the outer wall increased from 4.0% to 35.0%. For the remaining 600 epochs, the percentage continued to rise to ~70%. These sequential changes in learning rate pattern, suggests that this 3D network learns to decipher the aorta by first determining the location of the lumen and working outward to define the outer wall. FIG. 11 illustrates the results of this training loop. These results indicate for the first time the ability to extract the entirety of an aorta from the root to the iliac bifurcation and automatically differentiate the outer aneurysmal wall 150 from the inner aortic lumen 130.

A study performed by the inventors will now be described, with reference to FIGS. 12-26. Subtitles and headings in what follows have been included for readability only and are not intended to limit the scope of the invention, which is defined by the claims.

In this study, a modified U-Net architecture, as per FIG. 10, was implemented to achieve high-throughput, automated segmentation of blood vessels in CT images acquired with or without the use of contrast agent. In contrast enhanced CT images, the modified U-Net architecture further enabled simultaneous segmentation of both the arterial wall and blood flow lumen to enable characterization of the pathological contents. The efficacy of this U-Net architecture is demonstrated further below by reconstructing the thoracic and abdominal aorta, which is the main artery bringing blood supply from the heart to the rest of the body.

Methods

CT Images from a Clinical Cohort

Computerized Tomographic scans of the chest and abdomen were acquired through the Oxford Abdominal Aortic Aneurysm (OxAAA) study. The study received full regulatory and ethics approval from both Oxford University and Oxford University Hospitals (OUH) National Health Services (NHS) Foundation Trust (Ethics Ref 13/SC/0250). As part of the routine pre-operative assessment for aortic aneurysmal disease, a non-contrast CT of the abdomen and a CT angiogram (CTA) of both the chest and abdomen was performed for each patient. CTA images were obtained following contrast injection in helical mode with a pre-defined slice thickness of 1.25 mm. Non-contrast CT images included only the descending and abdominal aorta and were obtained with a pre-defined slice thickness of 2.5 mm.

Paired contrast and non-contrast CT images were anonymized within the OUH PACS system before being downloaded onto the secure study drive.

Manual Segmentation of CT Images

Twenty-six patients with paired non-contrast and CTA images of the abdominal region were randomly selected. In the CTA, both the aortic inner lumen and outer wall were segmented from the aortic root to the iliac bifurcation using the ITK-Snap segmentation software.

Semi-automatic segmentation of the aortic inner lumen was achieved using a variation of region-growing by manually delimiting the target intensities between the contrast-enhanced lumen and surrounding tissue. Segmentation of the aortic outer wall was performed manually by drawing along its boundary using the previously obtained inner lumen as a base. Removing the inner lumen from the larger outer wall segmentation results in a segmentation mask highlighting the content between the arterial wall and blood lumen (in this case, thrombus). In the non-contrast CT image, the aorta was manually segmented.

Figure 12:
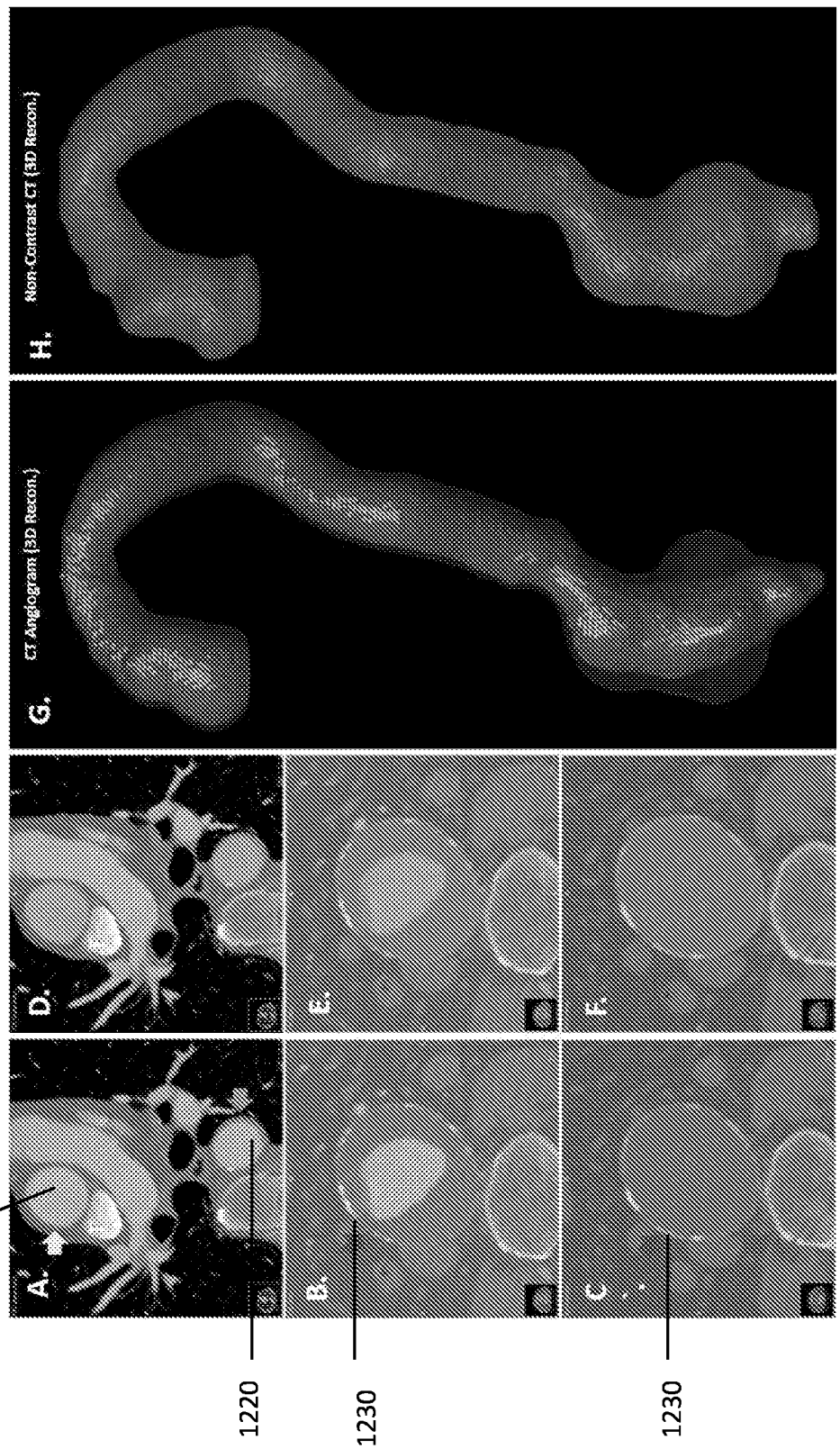
FIG. 12 shows axial slices from a contrast enhanced CT angiogram and a non-contrast scan and also shows overlaid manually segmented masks, and 3D reconstructed volumes generated from the segmentation masks.

Panels A-F of FIG. 12 depict axial slices from the CT of chest and abdomen. Panels A and B are CTA images depicting the ascending thoracic aorta 1210 (yellow arrow, panel A), descending thoracic aorta 1220 (blue arrow, panel A), and abdominal aorta 1230 (red arrow, panel B) which is aneurysmal and contains crescentic layers of thrombus. Panel C shows the corresponding cross section of the abdominal aorta 1230 (red arrow, panel C) in the non-contrast CT scan. The aortic contour is manually segmented using IKT snap. Panels D, E and F, show respectively the CT images of panels A, B and C with the overlying manually derived segmentation. Views of the 3D volumes of the aorta derived from the manual 2D segmentations are depicted in Panels G and H. Panel G shows the reconstructed aorta from the segmentations of the contrast CT images, and panel H sows the reconstructed aorta from the segmentations of the NCT images.

Assessment of Intra- and Inter-Observer Variation of Manual Segmentation

A subset of these scans was selected randomly for intra- and inter-observer variability evaluation (n=10). This directly assessed the validity and accuracy of the manual segmentations used for subsequent analysis. For the intra-observer assessment, manual segmentation of the 10 scans was performed for the second time after a gap of 2 weeks. For the inter-observer assessment, a trained clinician performed the segmentations independent of the primary observer. In both instances, segmentation masks were compared against the ground truth (observer 1).

Data Augmentation

Of the 26 patients, 13 patients were randomly allocated to the training ($n_{train}$=10) and validation cohorts ($n_{valid}$=3). Following manual segmentation, the original CT images and their corresponding image masks of only patients in the training/validation cohorts were augmented using divergence transformations. In order to diversify the training data set, divergence transformations employ nonlinear warping techniques to each axial slice, which manipulate the image in a certain predefined location. In panel A of FIG. 13, the aneurysmal sac can be seen towards the base of the gaussian peak and is noticeably stretched. By selecting the shape of the 3D surface, different warping affects can be created. In order to create localized stretching (Panel B of FIG. 13) a 2D gaussian curve is used:

$$g(i, j) = \exp\left[-\frac{(i - I_C)^2 + (j - J_C)^2}{2\sigma^2}\right]$$

Figure 13:
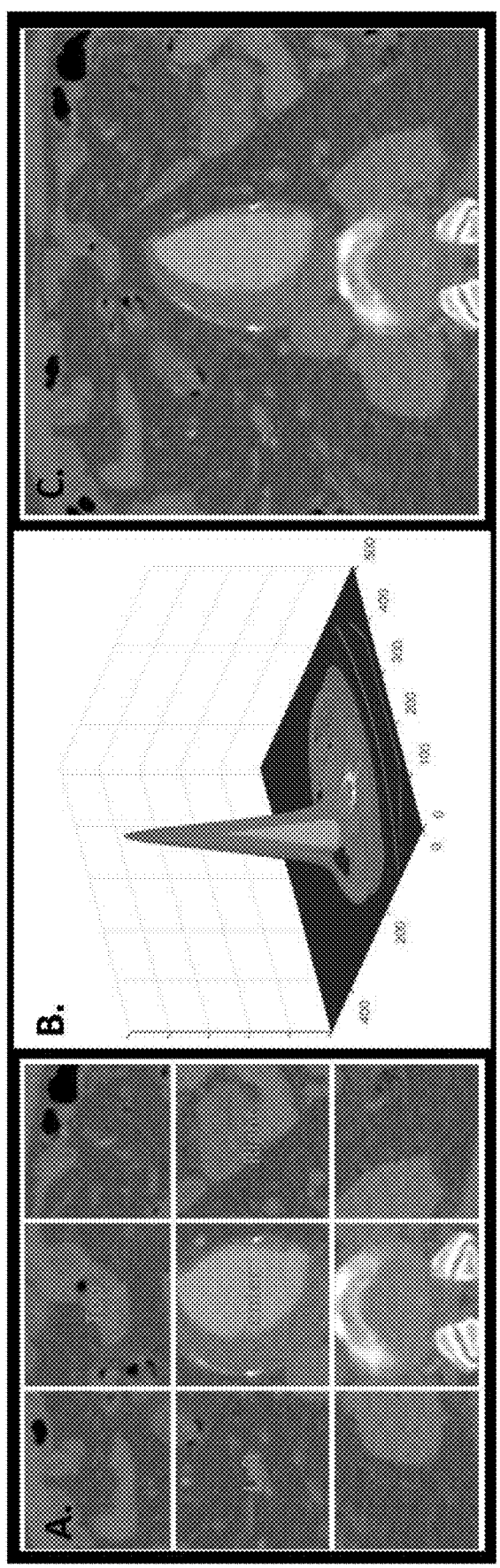
FIG. 13 shows an axial slice from a contrast-enhanced CT scan with predefined locations for the divergence transformation function (panel A), a visualisation of the non-linear warping applied (panel B) and an example augmented axial slice following a divergence transformation (panel C)
Figure 15A:
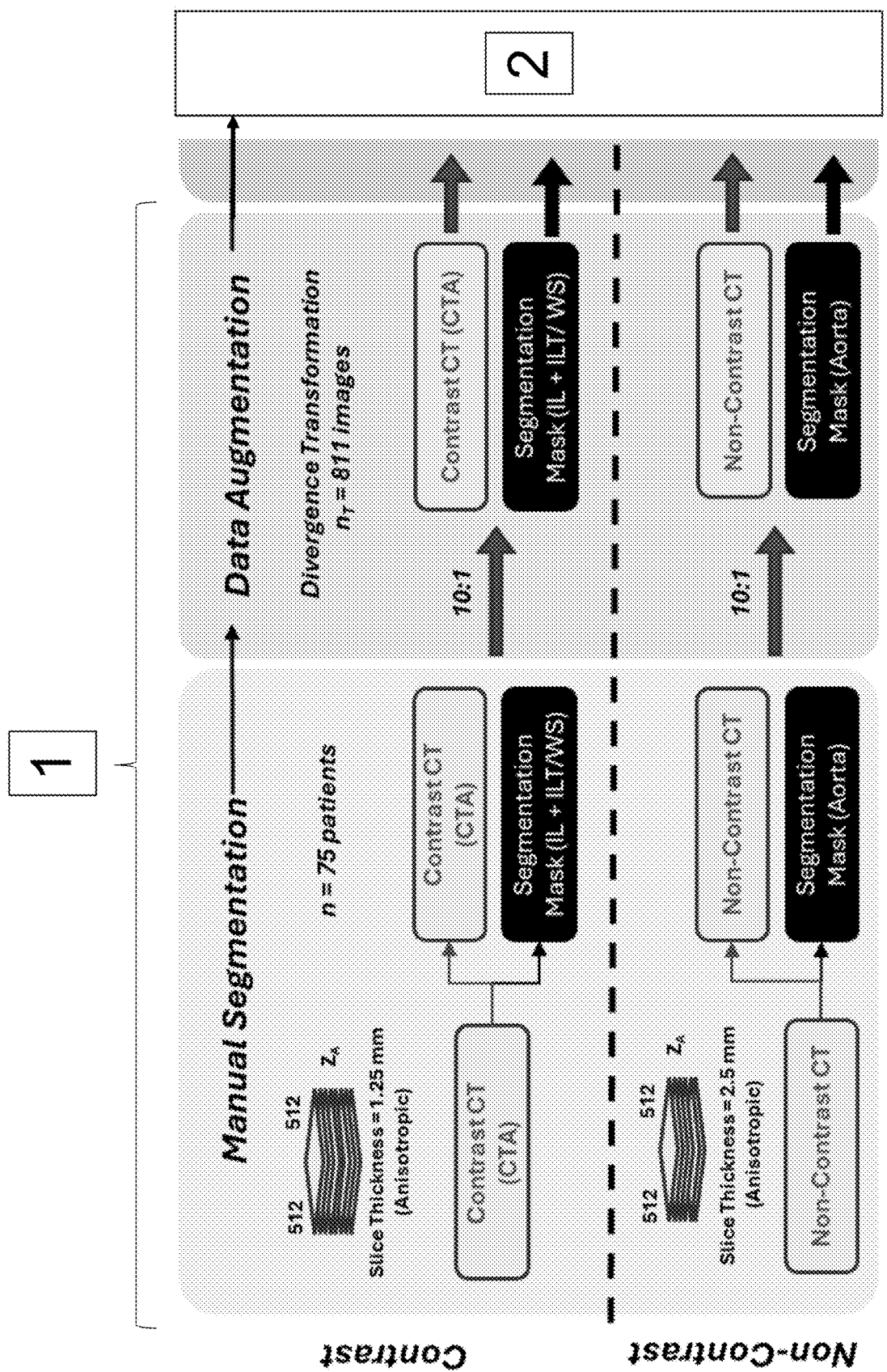
FIG. 15 shows a schematic of the automatic high resolution aortic segmentation pipeline used herein for the simultaneous detection of the aortic inner lumen, and intraluminal thrombus/outer wall (panel A), and the attention gated U-Net architecture used in the pipeline (panel B and duplicated from FIG. 10)
Figure 15A:
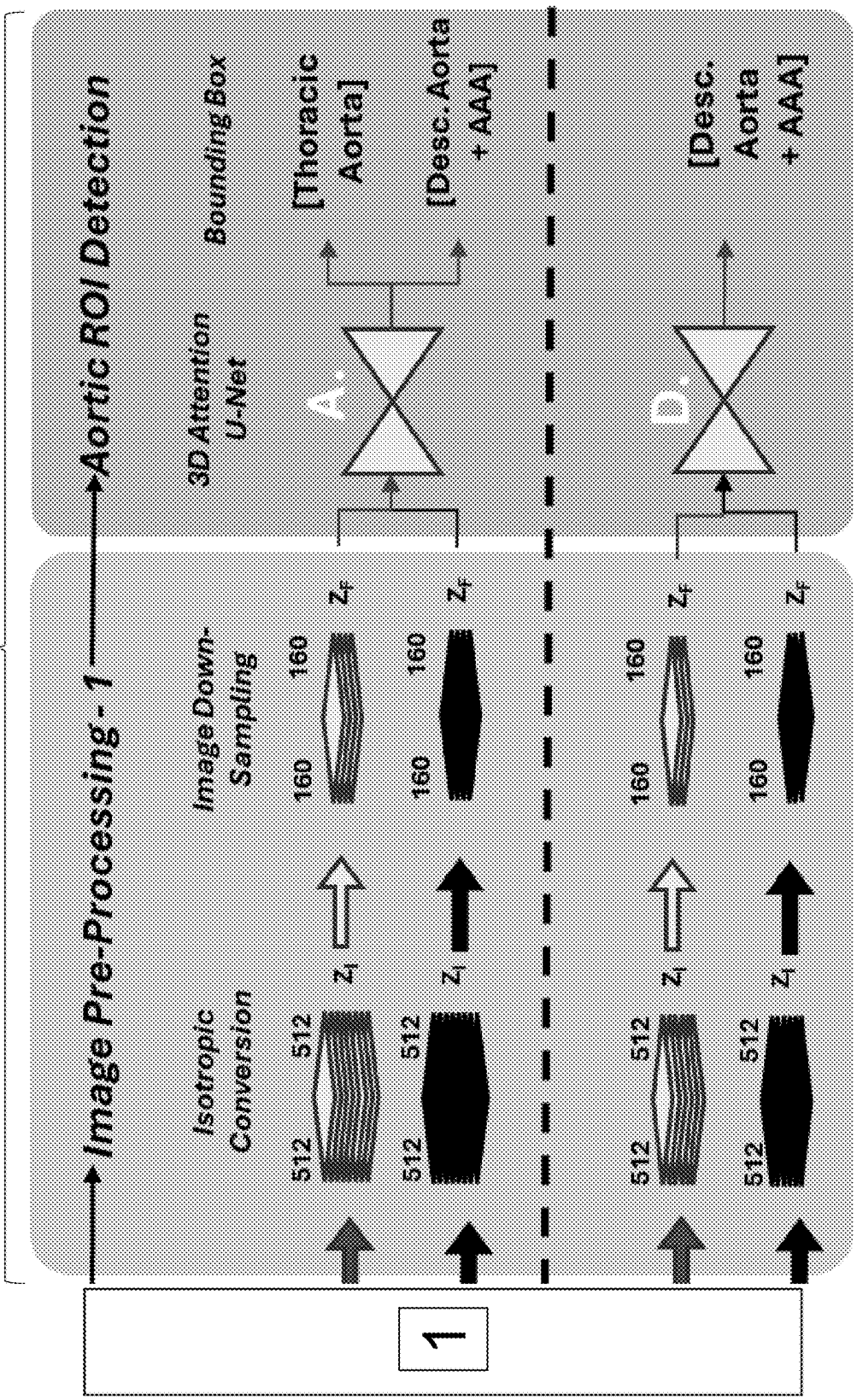
Figure 15A:
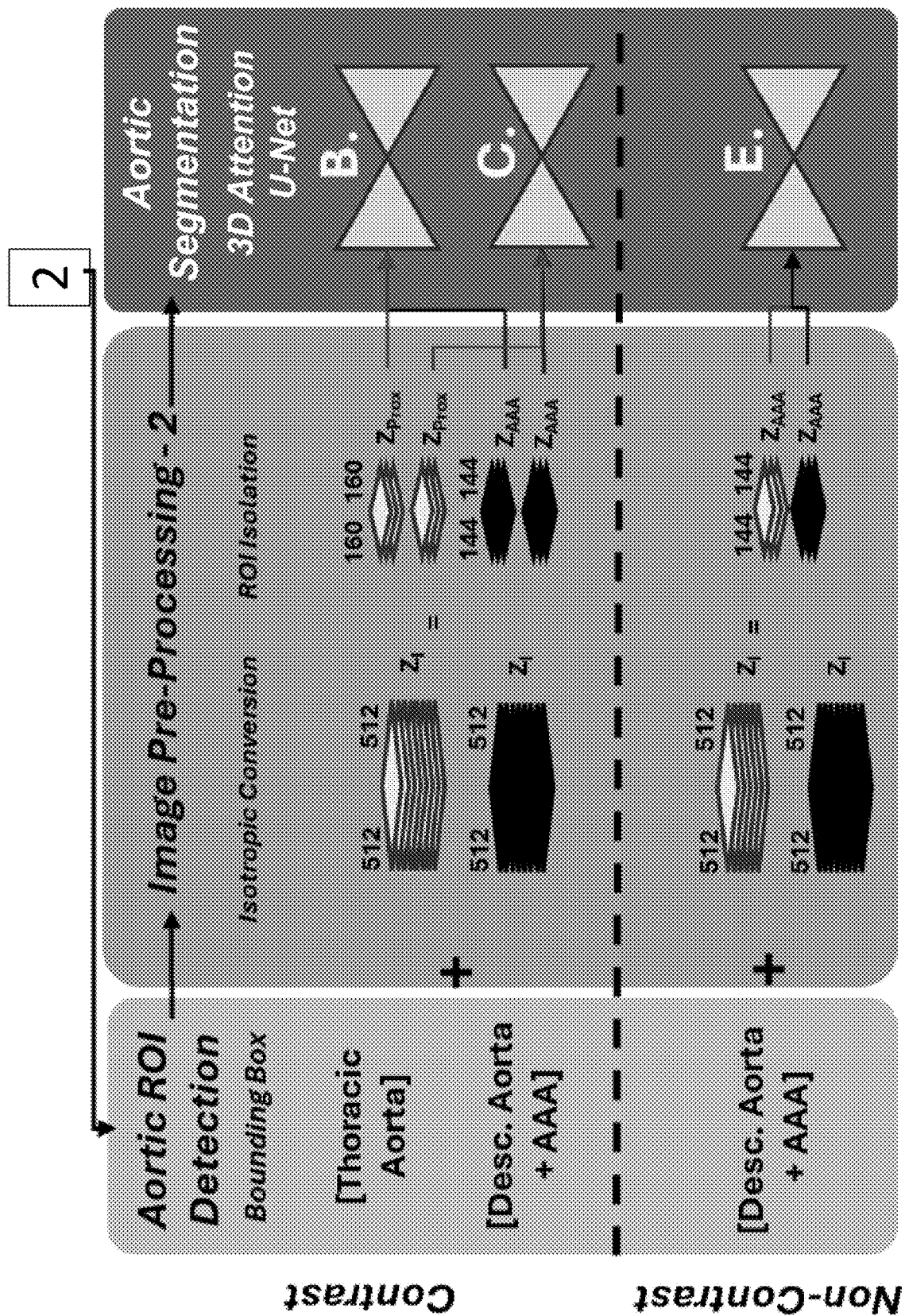
Figure 15B:
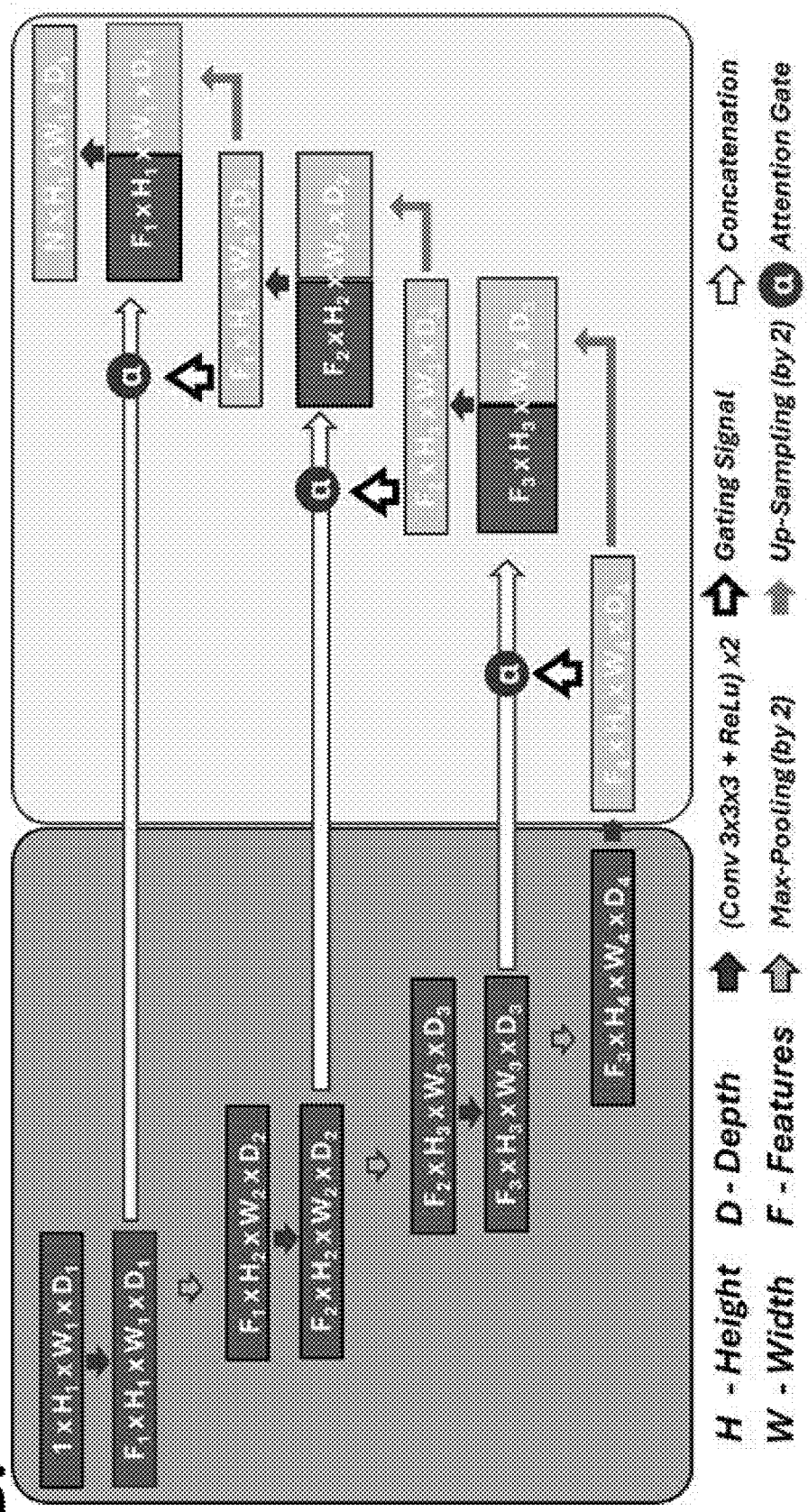

Here ($I_C$, $J_C$) is the centre from which the image is locally stretched. The images were augmented in this manner with gaussians at 5 locations adjacent to the aorta (indicated in panel A). Panel C of FIG. 13 shows an augmented axial slice following a divergence transformation. This method was extended to achieve both congruent and divergent local transformations. Therefore, each patient's scan in the training cohort was augmented 10:1 to obtain a total of 143 post-augmented scans. During training, each 3D image was augmented further using random rotation (0-15°), translation and scaling (0.7-1.3).

As seen in the table of FIG. 14, post-augmented scans were split based on the original pre-augmented images into training ($n_{train}$=10 patients, 110 augmented scans), and validation ($n_{valid}$=3 patients, 33 augmented scans) groups. This was done to avoid data leakage or the intermingling of patients and their augmented scans in the training/validation groups. Here, the validation group was used at the end of each training epoch to gauge model performance and fine-tune model hyperparameters. The remaining 13 patients formed the testing cohort ($n_{test}$=13).

U-Net Architecture

Panel A of FIG. 15 shows the high-resolution segmentation pipeline for the simultaneous detection of the aortic inner lumen and intra-luminal thrombus/outer wall. In this study, a variation of the U-Net was utilized for both the Aortic Region-of-interest (ROI) detection and segmentation tasks. As discussed previously in relation to FIG. 10, the general architecture of the U-Net comprises two components: the contraction path and expansion path (FIG. 15, Panel B). The contraction path serves to extract information and capture the context of the input at the expense of losing spatial information. Here, as the input CT image (CTA/Non-Contrast) is deconstructed, it is able to extract more complex features relevant to the aortic segmentation task. This is followed by an expansion path, where the size of the image gradually increases to produce a predictive binary mask. The lost spatial information is restored using skip connections and is merged via concatenation. These connect the output of the down-sampling path with the extracted feature maps/ input of the up-sampling path at the same level. This serves to integrate the spatial and contextual information to assemble a more precise prediction of the aortic structure.

Attention Gating

The use of a 3D U-Net with attention gating was evaluated against a generic 3D U-Net for segmentation of the aorta. Information extracted from the coarse scale is used within this gating mechanism to filter out irrelevant and noisy data exchanged via the skip connections before the concatenation step. The output of each attention gate is the element-wise multiplication of input feature-maps and a learned attention coefficient [0-1]. Given that we are simultaneously predicting the location of the aortic inner lumen and outer wall, multi-dimensional attention coefficients were used to focus on a subset of target structures. The gating coefficients were determined using additive addition, which has been shown to be more accurate than multiplicative addition.

FIG. 15, panel B illustrates the 3D U-Net architecture with the attention gates utilized in this study. The architecture is the same as that described above in relation to FIG. 10. The initial learning rate and weight decay for both models were set to $1.0 \times 10^{-3}$ and $1.0 \times 10^{-6}$, respectively. Training to segment the aneurysmal region was carried out for a total of 1000 epochs with a batch size of 2 3D Images.

Loss Function

To quantify the performance of the algorithm at each step, the DICE score was utilized. The DICE score is a well-known performance metric in image segmentation tasks. This metric gauges the similarity between two images (A and B) and is defined as follows:

$$\mathrm{DICE}(A, B) = \frac{2|A \cap B|}{|A| + |B|}$$

Aortic Segmentation Pipeline: Aortic ROI Detection

Following data augmentation, all images were pre-processed. Pre-processing steps included isotropic voxel conversion and image down-sampling by a factor of 3.2 (512× 512×$Z_i$→160×160×$Z_f$). This was performed to allow for increased efficiency during model training. The next step in this automatic aortic segmentation pipeline is Aortic ROI detection. This was performed on both the contrast and non-contrast CT images to isolate the aortic region for subsequent segmentation.

Attention U-Nets A and D (labelled "Attn U-Net A" and "Attn U-Net D" in the table of FIG. 16) were trained for a total of 600 epochs to segment the aorta from these decreased resolution, isotropic CTA and non-contrast CT images, respectively. The initial learning rate, weight decay, and batch-size for model training were set respectively to $1.0 \times 10^{-3}$ and $1.0 \times 10^{-6}$ and 2 3D Images. Aortic bounding boxes were generated from the predicted segmentation masks. Two bounding boxes were generated from the contrast CT image (1. Aortic Arch and 2. Descending Aorta and AAA) and one was generated from the non-contrast CT image (1. Descending Aorta and AAA). Regions of interests (144×144×[$Z_{AA}$ or $Z_{AAA}$]) centred around the defined bounding box were isolated and served as the input data for aortic segmentation.

Aortic Segmentation Pipeline: Aortic Segmentation

U-Nets B and C (labelled respectively "Attn U-Net B" and "Attn U-Net C" in the table of FIG. 16) were trained for 1500 epochs on the CTA CT ROIs. They were tasked to simultaneously segment the aortic inner lumen and ILT/ outer wall regions of the aortic arch and descending aorta/

AAA, respectively. On the other hand, U-Net E (labelled "Attn U-Net E" in FIG. 16) was trained for 1000 epochs on the non-contrast ROIs and was tasked to segment the descending aorta/AAA. The learning rate, weight decay, and batch-size for all U-Nets were set to $1.0 \times 10^{-3}$ and $1.0 \times 10^{-6}$ and 2 3D Images, respectively.

The table of FIG. 16 summarises all the U-Nets trained and evaluated in this study. Model training was performed simultaneously on a workstation with 2 11 gb NVIDIA RTX 2080 TI graphics cards. Following training, in order to assess model performance and generalizability, models were evaluated on an external test cohort of non-augmented CTA and non-contrast images ($n_{ext}$=13 scans). This cohort of scans was obtained from the same patient population and was independent of the scans used during training.

Results

CT Image Characteristics

Of the cases (n=26) included in the study, 13 were used for model training and the remaining 13 used for model testing. Details regarding the CT image characteristics between these groups are summarized in the table of FIG. 17.

Intra- and Inter-Observer Variability Assessment

There were strong agreements for both inter- and intra-observer measurements (intra-class correlation coefficient, 'ICC'=0.995 and 1.00, respective. P<0.001 for both). The table of FIG. 18 summarises the DICE score metrics for the intra- and inter-observer variability assessments performed on CTA and non-contrast CT images. The inter-operator variability is greater than intra-operator variability for all regions, as seen by the lower DICE scores. These data supports the accuracy of the manual segmentations used for model training.

Attention-Based 3D-U-Net Vs 3D-U-Net for AAA Segmentation

Figure 19:
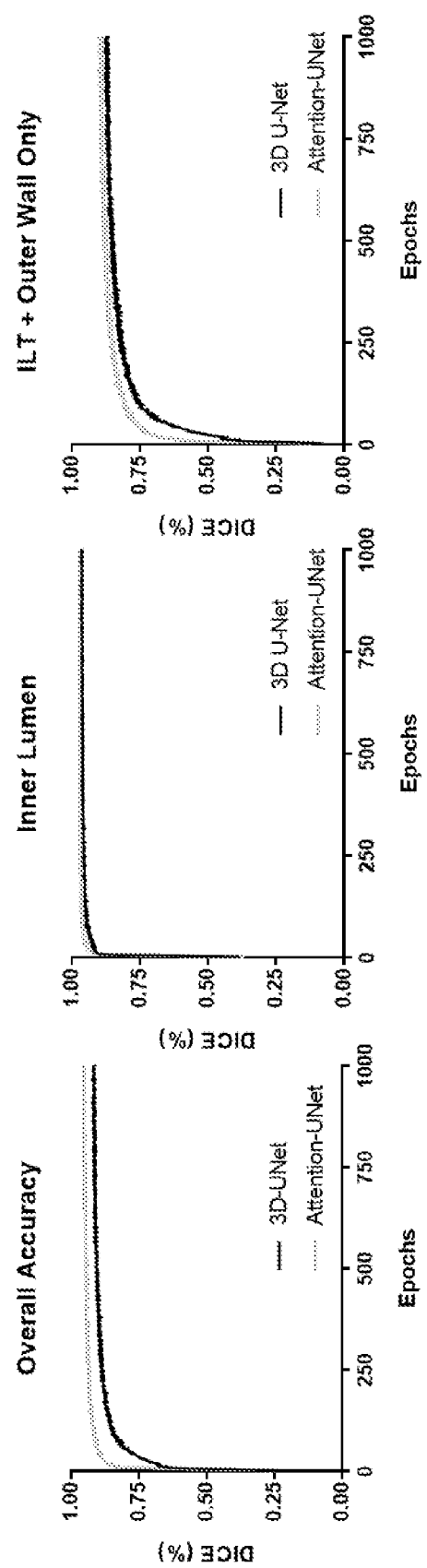
FIG. 19 shows several graphs of the DICE scores for several model outputs as compared against the ground truth segmentations.

To assess the benefit of attention-gating for AAA segmentation, the performance of an attention-based 3D U-Net was compared against that of a generic 3D U-Net. FIG. 19 illustrates the evolving DICE score metric for the validation group during model training. Specifically, the left hand graph of FIG. 19 relates to the overall accuracy of the models as quantified by the DICE score, the middle graph relates to the DICE score for determining the inner lumen, and the right hand graph relates to the DICE score for determining the ILT and outer wall only. During the training of the Attention-based U-Net, the overall DICE score increased from 24% at epoch 1 (Inner Lumen: 36.7%, Outer Wall: 11.9%) to approximately 95.3% at epoch 1000 (Inner Lumen: 97.4%, Outer Wall: 89.2%). On the other hand, the performance of the control 3D U-Net increased from 23.0% at epoch 1 (Inner Lumen: 38.2%, Outer Wall: 7.7%) to approximately 91.8.0% at epoch 1000 (Inner Lumen: 96.4%, Outer Wall: 87.2%).

Segmentation of the testing cohort was used to evaluate model performance. Model output was compared against the manually segmented ground-truth images utilizing the DICE score metric. The results of this analysis are found in the table of FIG. 20. The accuracy of the Attention-based U-Net in extracting both the inner lumen and the outer wall of the aneurysm is superior to that of the generic 3D-U-Net. This rationalizes the incorporation of the attention-gating unit into the segmentation pipeline.

Figure 21:
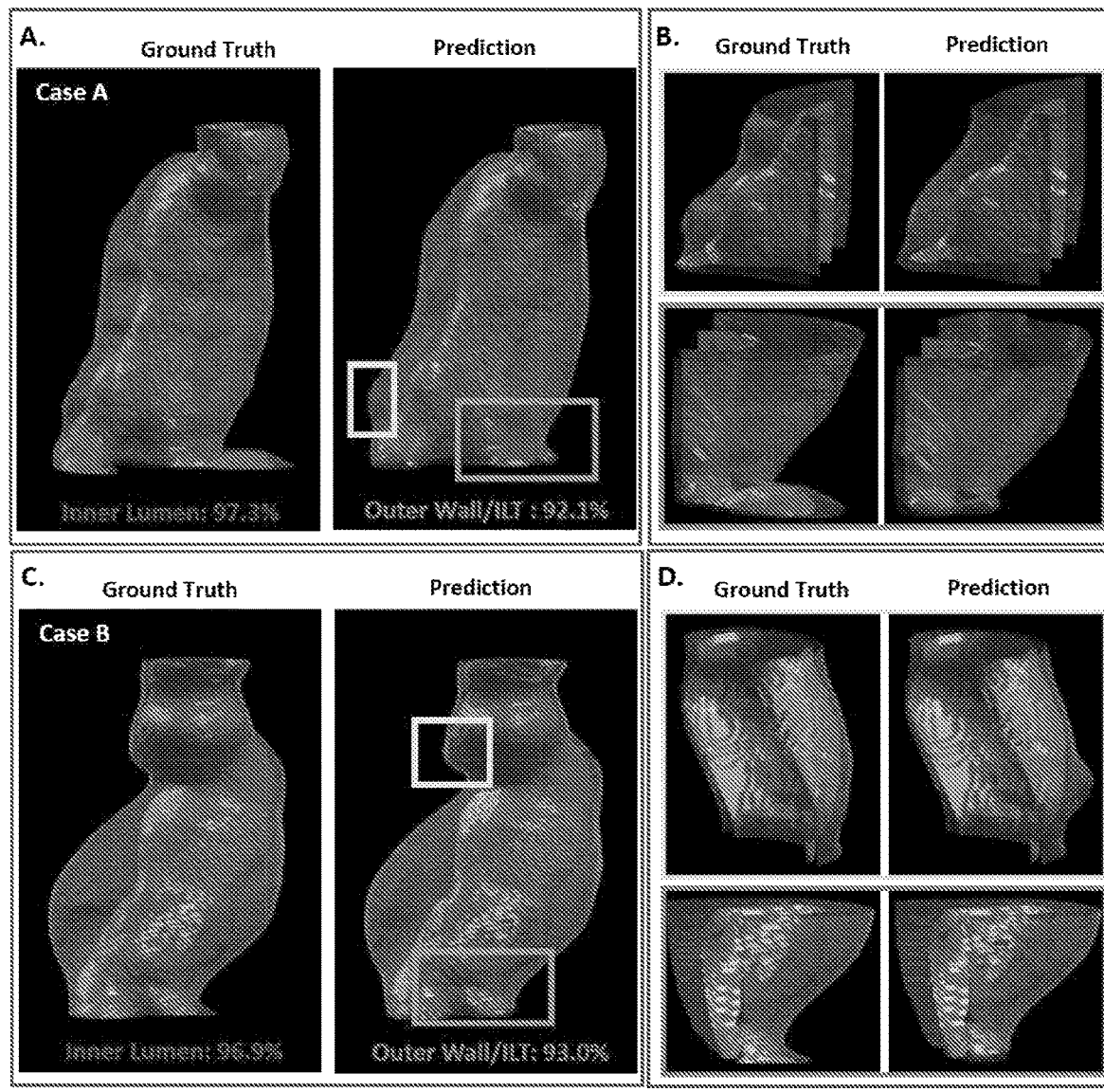
FIG. 21 shows attention-based U-Net outputs for two patients with labelled ground truth masks and corresponding DICE scores.

Panels A and C of FIG. 21 show attention-based 3D-U-Net outputs for two patients within the test set along with their respective ground truths (labelled segmentations masks) and DICE similarity scores. Areas of discrepancy arise at the iliac bifurcation and at other points of high curvature (panels B and D of FIG. 21).

Aortic Segmentation from CTA Images

Figure 22:
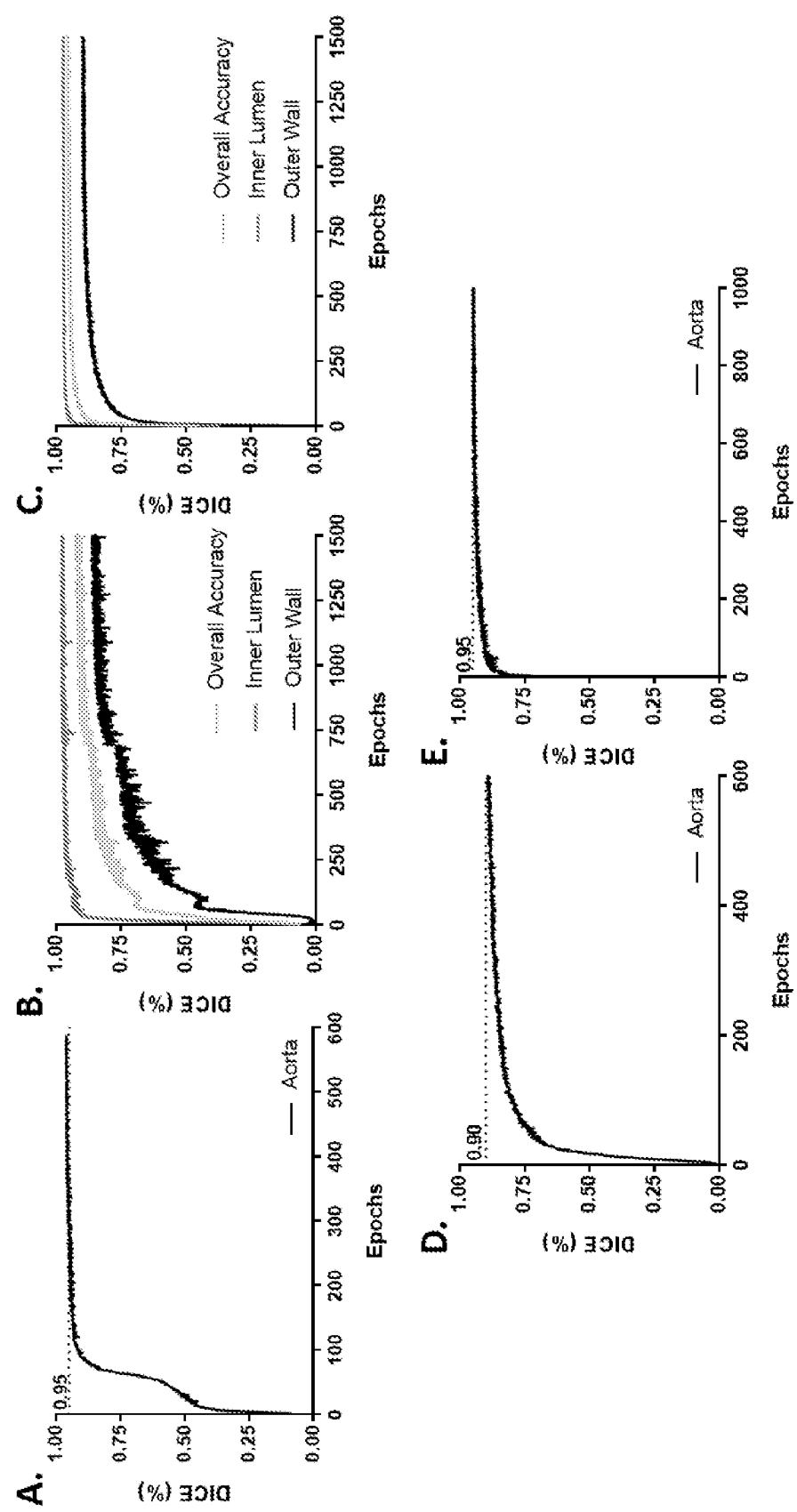
FIG. 22 shows graphs, for each of the five U-Nets studied, of the DICE score for the validation cohort against epoch.
Figure 24:
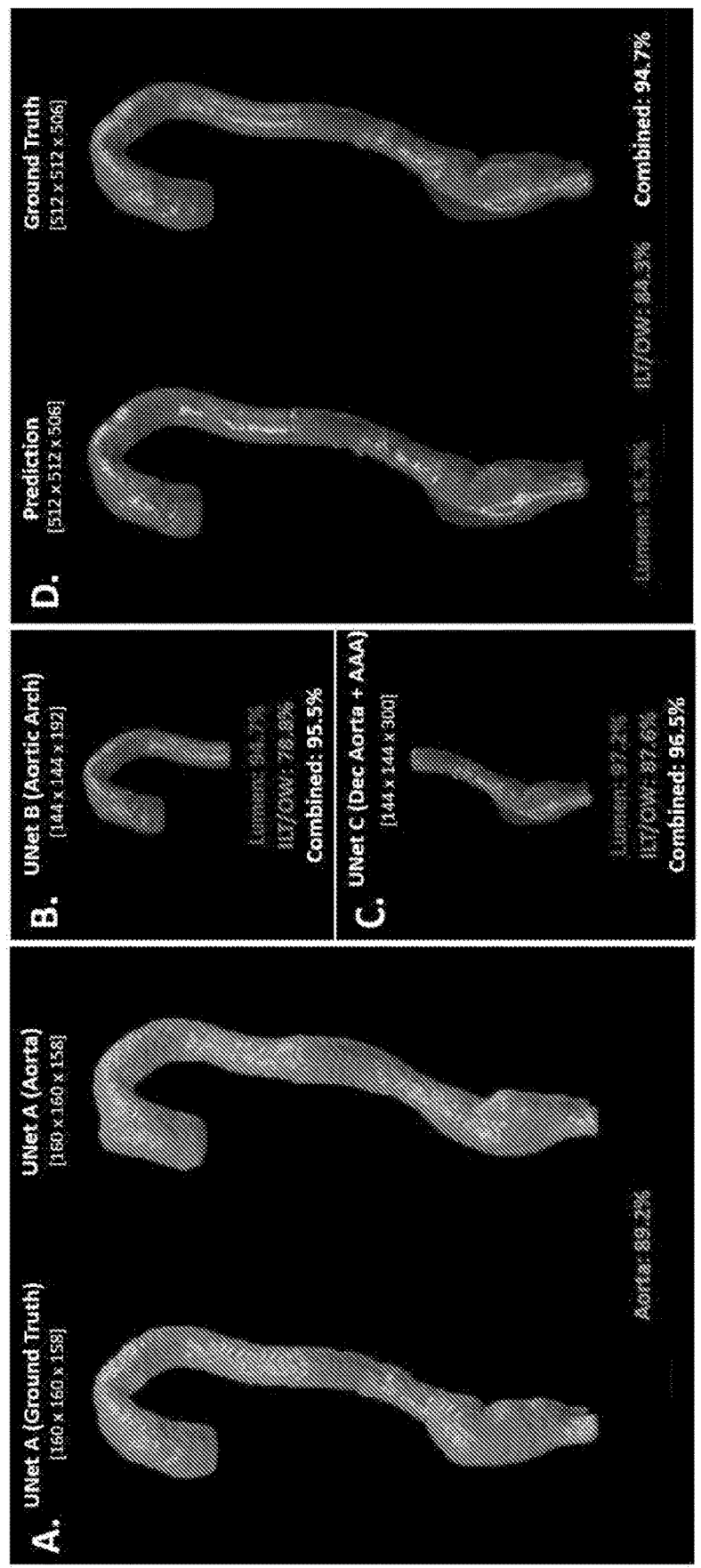
FIG. 24 shows visualisations of the 3D volume output from attention-based U-Nets A-C from a contrast-enhanced CT image for a patient within the testing cohort, and the corresponding ground truth 3D volumes.

Panels A-C of FIG. 22 illustrate the evolving DICE score metric for the validation group during training of Attn U-Nets A-C involved in the segmentation of the aorta from contrast-enhanced CTA images. Attn U-Net A was trained for 600 epochs on down-sampled CT images. Attn U-Nets B and C were trained for 1500 epochs on the ROIs derived from Attn U-Net A—aortic arch (panel B) and descending aorta/AAA (panel C). The table of FIG. 23 displays the performance of Attn U-Nets A-C on the ability to segment CTA images within the testing cohort via the DICE score metric. Merging the outputs of Attn U-Nets B and C to generate the entire aortic volume prediction results in an overall DICE Score accuracy of 93.0±0.6% (Inner Lumen: 96.4±0.3%, Outer Wall: 87.3±0.9%). FIG. 24 show the model predictions for Attn U-Nets A-C for a patient within the external test cohort compared against their respective ground truth annotations. Panel A of FIG. 24 shows the ground truth and model prediction for Attn U-Net A. Attn U-Net A identified the aortic structure from down-sampled images and was the basis for ROI detection. Attn U-Nets B and C (panels B and C respectively) identified both the inner lumen and outer wall predictions for their indicated region (aortic arch for Attn U-Net B and descending aorta and AAA for Attn U-Net C). Panel D of FIG. 24 shows the merged/combined volume prediction of U-Nets B and C along with the ground truth.

Aortic Segmentation from Non-Contrast CT Images

Figure 26:
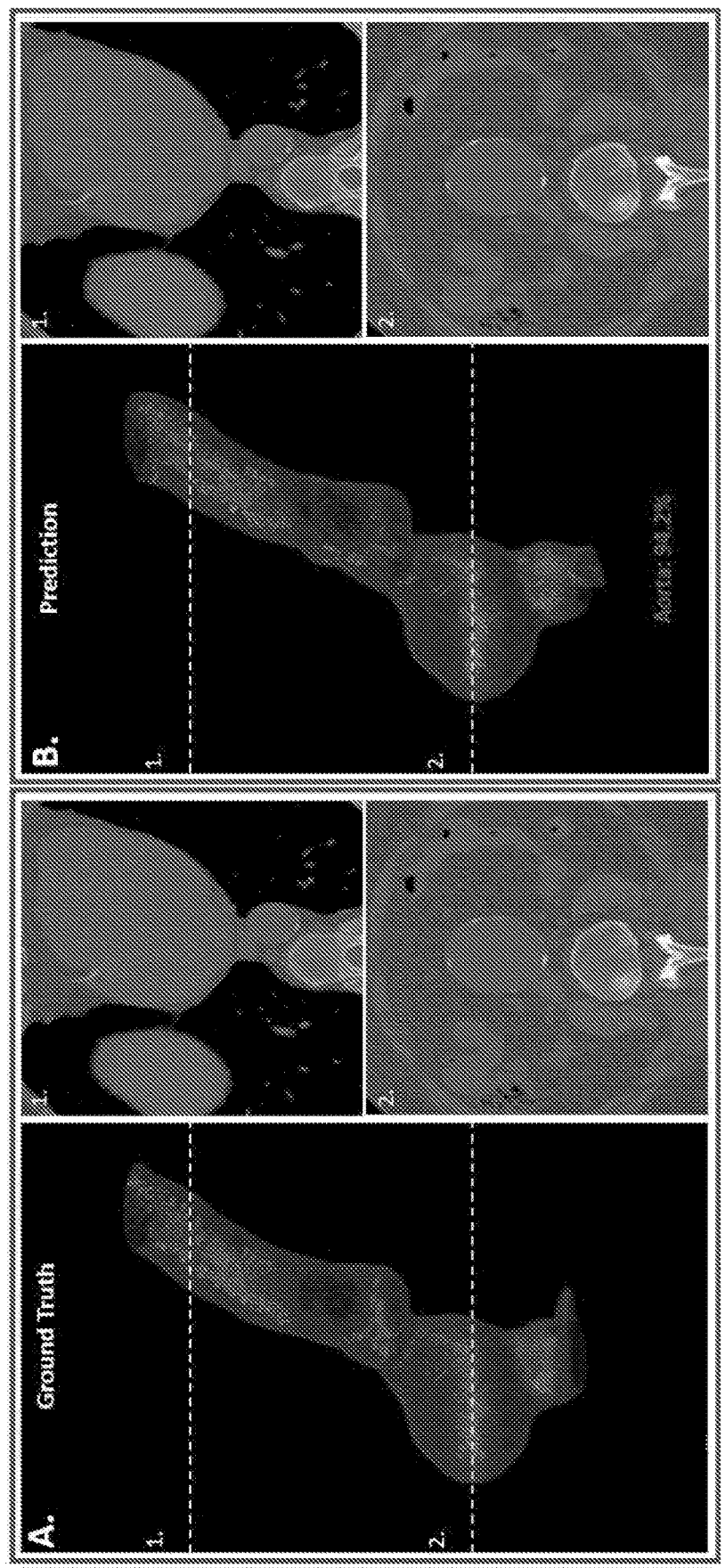
FIG. 26 shows visualisations of the 3D volume output from attention-based U-Nets D-E from a non-contrast CT image for a patient within the testing cohort, and the corresponding ground truth 3D volumes.

Panels D and E of FIG. 23 illustrate the evolving DICE score metric for the validation cohort during training of Attn U-Net D and Attn U-Net E, which are involved in the segmentation of the aorta from non-contrast CT images. The table of FIG. 25 displays the performance of Attn U-Net D and Attn U-Net E on the ability to segment non-contrast CT images within the testing cohort via the DICE score metric. FIG. 26 shows the results of the automated aortic segmentation pipeline (FIG. 15) of a non-contrast CT image for a patient within the testing cohort (Attn U-Nets D and E). Panel A of FIG. 26 shows the manually segmented aorta (ground truth). Panel B of FIG. 26 shows a visualization of the aortic segmentation results as predicted by Attn U-Net E. Two regions within the (1.) thoracic region and (2.) aneurysm have been highlighted in the images.

The above discussed study has demonstrated a fully automatic and high-resolution algorithm that is able to extract the aortic volume from both CTA and non-contrast CT images at a level superior to that of other currently published methods. The extracted volume can be used to standardize current methods of aneurysmal disease management and sets the foundation for subsequent complex geometric analysis. Furthermore, the proposed pipeline can be extended to other vascular pathologies.

Furthermore, the above study has demonstrated the ability to use a deep learning method to isolate the aorta from a non-contrast CT scan. This will allow for the extraction of complex morphological information from non-contrast images and subsequent longitudinal analysis. The same methodology underpinning this work can be extended to enable automatic segmentation of other hollow or solid organs (such as the kidneys, veins, liver, spleen, bladder, or bowel) with or without the use of intravenous contrast agents.

Figure 27:
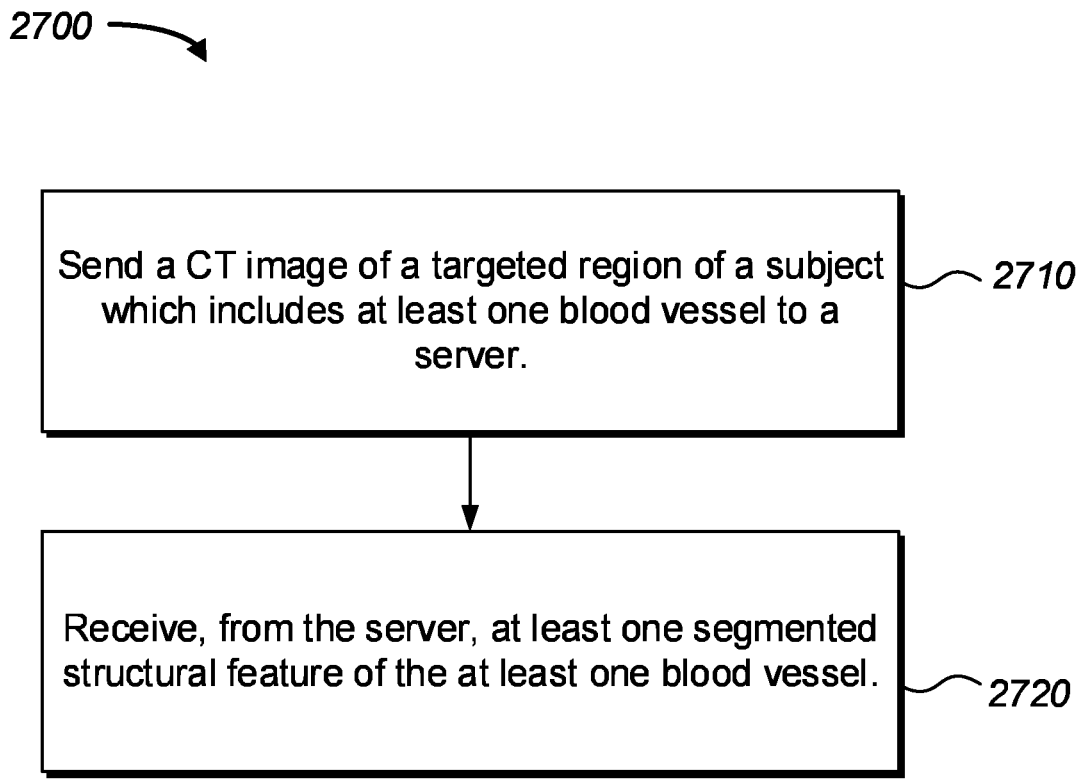
FIG. 27 shows a flowchart.

FIG. 27 shows a flowchart of a method for obtaining at least one segmented structural feature from a CT image.

At step 2710, the method comprises sending a CT image to a server, where the CT image comprises a targeted region of a subject including at least one blood vessel. The server may contain instructions for segmenting structural features of a blood vessel in a CT image.

At step 2720, the method comprises receiving, from the server, receiving, from the server, at least one segmented structural feature of the at least one blood vessel.

The method for obtaining at least one segmented structural feature from a CT image, as described above in relation to FIG. 27, is suitable for performance by a computing apparatus such as computing apparatus 600 as shown in FIG. 6.

Figure 28:
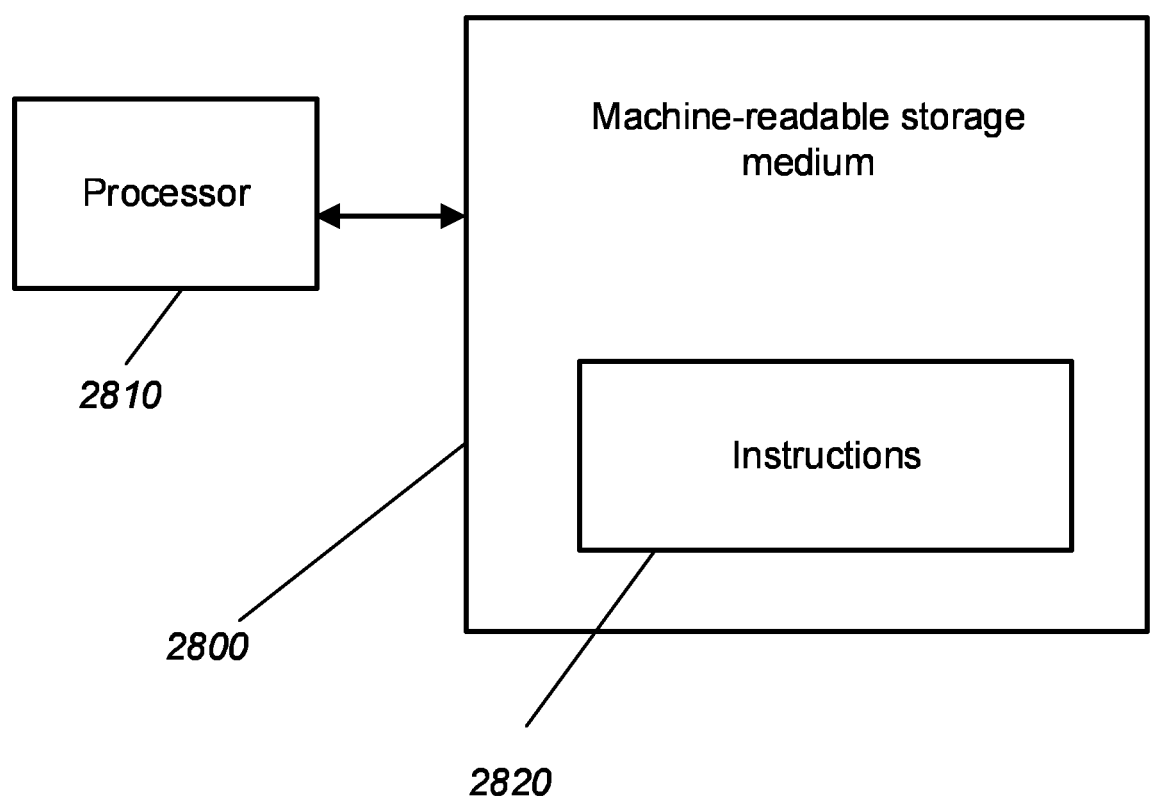
FIG. 28 is a block diagram of a machine-readable medium according to some examples.

FIG. 28 illustrates a computer readable medium 1200 according to some examples. The computer readable medium 2800 stores units, with each unit including instructions 2820 that, when executed, cause a processor 2810 or other processing/computing device or apparatus to perform particular operations.

The computer readable medium 2800 may include instructions 2820 that, when executed, cause a processing device 2810 to, train a machine learning image segmentation algorithm, using a plurality of CT images and a corresponding plurality of segmentation masks, to learn features of the CT images that correspond to structural features of blood vessels labelled in the segmentation masks, and output a trained image segmentation model which is usable for segmenting structural features of a blood vessel in a CT image.

The machine readable medium 2800 may additionally or alternatively comprise instructions 2820 to provide a CT image to a trained image segmentation model, the trained image segmentation model trained to learn features of CT images that correspond to structural features of blood vessels and to segment, using the trained image segmentation model, at least one structural feature of a blood vessel in the provided CT image.

The machine readable medium 2800 may additionally or alternatively comprise instructions 2820 to receive a plurality of CT images, each CT image showing a targeted region of a subject, the targeted region including at least one blood vessel. The machine readable medium 2800 may additionally comprise instructions 2820 to segment the plurality of CCT images to generate a corresponding plurality of segmentation masks, where each segmentation mask labels at least one structural feature of the at least one blood vessel in the corresponding CCT image.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine-readable storage storing such a program. Still further, embodiments of the present invention may be conveyed electronically via any medium such as a communication signal carried over a wired or wireless connection and embodiments suitably encompass the same.

Many variations of the methods described herein will be apparent to the skilled person. For example, the methods described herein can be used to identify/segment features in other blood vessels besides the aorta (e.g. other arteries or veins). Furthermore, the methods described herein can be used to analyse the behaviour of other organs, for example in the liver, spleen, or kidney.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method for training a machine learning image segmentation algorithm to segment structural features of a blood vessel in a computed tomography (CT) image, the method comprising:
   receiving a labelled training set for the machine learning image segmentation algorithm, the labelled training set comprising:
      a plurality of CT images, each CT image of the plurality of CT images showing a targeted region of a subject, the targeted region including at least one blood vessel; and
      a corresponding plurality of segmentation masks, each segmentation mask labelling at least one structural feature of a blood vessel in a corresponding CT image of the plurality of CT images;
   training a machine learning image segmentation algorithm, using the plurality of CT images and the corresponding plurality of segmentation masks, to learn features of the CT images that correspond to structural features of the blood vessels labelled by the segmentation masks, and output a trained image segmentation model; and
   outputting the trained image segmentation model usable for segmenting structural features of a blood vessel in a CT image.

2. A method according to claim 1, wherein the at least one blood vessel of the targeted region of the CT image includes the aorta, or
   wherein the targeted region of the CT image includes an aortic aneurysm, or,
   wherein the structural features of the blood vessel comprise one or more of: inner lumen, outer wall, intima/media, false lumen, calcification, thrombus, ulceration, atherosclerotic plaques, or
   wherein the blood vessel comprises an artery, or
   wherein the blood vessel comprises a vein.

3. A method according to claim 1, wherein the computed tomography (CT) image includes a contrast CT image (CCT) or a non-contrast CT image (NCT).

4. A method according to claim 1, wherein the method further comprises generating the labelled training set.

5. A method according to claim 1, wherein the labelled training set has been established according to the method comprising:
- receiving a plurality of CCT images, each CCT image showing a targeted region of a subject, the targeted region including at least one blood vessel; and
- segmenting the plurality of CCT images to generate a corresponding plurality of segmentation masks, each segmentation mask labelling at least one structural feature of the at least one blood vessel in the corresponding CCT image;
- wherein the labelled training set includes pairs of CCT images and the corresponding segmentation masks.

6. A method according to claim 1, wherein the machine learning image segmentation algorithm comprises a neural network.

7. A method according to claim 1, wherein each segmentation mask of the plurality of segmentation masks comprises a binary segmentation mask.

8. A non-transitory computer-readable medium having instructions stored thereon which, when executed by one or more processors, cause the one or more processors to implement a method for training a machine learning image segmentation algorithm according to claim 1.

9. A computing apparatus for training a machine learning image segmentation algorithm to segment structural features of a blood vessel in a computed tomography (CT) image, the apparatus comprising:
- one or more memory units; and
- one or more processors configured to execute instructions stored in the one or more memory units to perform the method of claim 1.

10. A non-transitory computer-readable medium having stored thereon computer-readable code representative of the trained image segmentation model of claim 1.

11. A non-transitory computer-readable medium according to claim 10, the computer readable medium further having instructions stored thereon which, when executed by one or more processors, cause the one or more processors to implement a method comprising:
- providing a CT image to the trained image segmentation model, the trained image segmentation model trained to learn features of CT images that correspond to structural features of blood vessels; and
- segmenting, using the trained image segmentation model, at least one structural feature of a blood vessel in the provided CT image.

12. A method for segmenting structural features of a blood vessel in a computed tomograph (CT) image, the method comprising; providing the CT image to a trained image segmentation model, wherein the trained image segmentation model has been trained according to the method comprising:
- receiving a labelled training set for the machine learning image segmentation algorithm, the labelled training set comprising:
  - a plurality of CT images, each CT image of the plurality of CT images showing a targeted region of a subject, the targeted region including at least one blood vessel; and
  - a corresponding plurality of segmentation masks, each segmentation mask labelling at least one structural feature of a blood vessel in a corresponding CT image of the plurality of CT images;
- training a machine learning image segmentation algorithm, using the plurality of CT images and the corresponding plurality of segmentation masks, to learn features of the CT images that correspond to structural features of the blood vessels labelled by the segmentation masks, and output a trained image segmentation model; and
- outputting the trained image segmentation model usable for segmenting structural features of a blood vessel in the provided CT image; and
- segmenting, using the trained image segmentation model, at least one structural feature of a blood vessel in the provided CT image.

13. A non-transitory computer readable medium having stored thereon segmentation data generated using a method according to claim 12.

14. A computing apparatus for segmenting structural features of a blood vessel in a computed tomography (CT) image, the apparatus comprising:
- one or more memory units; and
- one or more processors configured to execute instructions stored in the one or more memory units to perform the method of claim 12.

15. A method comprising:
- sending a computed tomography (CT) image to a server, the CT image showing a targeted region of a subject including at least one blood vessel; and
- receiving, from the server, at least one segmented structural feature of the at least one blood vessel by performing the method of claim 12.

16. A computing apparatus configured to perform the method of claim 15.

* * * * *